US007892753B1

(12) United States Patent
Banerjee

(10) Patent No.: US 7,892,753 B1
(45) Date of Patent: Feb. 22, 2011

(54) DIAGNOSTIC AND THERAPEUTIC APPLICATIONS OF SOLUBLE LHCGR PROTEIN

(76) Inventor: Subhasis Banerjee, 36 Crescent Road, New Barnet, Herts (GB) EN4 9RF ( * ) Notice: Subject to any disclaimer, the term of this patent is extended or adjusted under 35 U.S.C. 154(b) by 405 days.

(21) Appl. No.: 11/578,547

(22) PCT Filed: Apr. 15, 2005

(86) PCT No.: PCT/GB2005/001473

§ 371 (c)(1),
(2), (4) Date: Sep. 4, 2007

(87) PCT Pub. No.: WO2005/100397

PCT Pub. Date: Oct. 27, 2005

(30) Foreign Application Priority Data

Apr. 15, 2004 (GB) ................................ 0408449.7

(51) Int. Cl.
*G01N 33/53* (2006.01)

(52) U.S. Cl. .......................... 435/7.1; 435/7.2; 436/518

(58) Field of Classification Search ....................... None
See application file for complete search history.

(56) References Cited

U.S. PATENT DOCUMENTS

| | | | |
|---|---|---|---|
| 4,946,778 | A | 8/1990 | Ladner et al. |
| 5,925,549 | A | 7/1999 | Hsueh et al. |
| 6,218,509 | B1 | 4/2001 | Igarashi et al. |
| 6,663,865 | B1 | 12/2003 | Borrelli et al. |

FOREIGN PATENT DOCUMENTS

WO WO-02061087 * 8/2002

OTHER PUBLICATIONS

Mackay et al Genetics 2003, vol. 163, p. 1365-1373.*

Kuno et al. J Biol. Chem 1993, vol. 268, p. 13510-13518.*

Asmun et al. Blood 1992, vol. 79, p. 3344-3349.*

Jane Reece "Molecular biology of Gene", Gillen editor, 4th edition, 1988, p. 342, p. 343, p. 442 and p. 445.*

Green et al. Pro. Natl. Acad. Sci. 1999 vol. 96, p. 4176-4179.*

Erlenbach et al. J. Biol Chem 2001 vol. 276, p. 29382-29392.*

Noutoshi et al. Journal 2005 vol. 43, p. 873-888.*

Bowie et al. Science, 1990 vol. 247:1306-1310.*

Abdallah, M.A., et al., "Human Fetal Nongonadal Tissues Contain Human Chorionic Gonadotropin/Luteinizing Hormone Receptors," *J. Clin. Endocrinol. Metab. 89*:952-956, The Endocrine Society (Feb. 2004).

Altschul, S.F., et al., "Basic Local Alignment Search Tool," *J. Mol. Biol. 215*:403-410, Academic Press Limited (1990).

Apaja, P.M., et al., "Luteinizing Hormone Receptor Ectodomain Splice Variant Misroutes the Full-Length Receptor into a Subcompartment of the Endoplasmic Reticulum," *Mol. Biol. Cell 17*:2243-2255, American Society for Cell Biology (May 2006).

Ascoli, M., et al., "The Lutropin/Choriogonadotropin Receptor, A 2002 Perspective," *Endocrine Rev. 23*:141-174, The Endocrine Society (2002).

Austgulen, R., et al., "Increased Levels of Soluble Tumor Necrosis Factor-α Receptors in Serum from Pregnant Women and in Serum and Urine Samples from Newborns," *Pediatr. Res. 33*:82-86, International Pediatric Research Foundation (1993).

Banerjee, S., et al., "Quantitative recovery of immunoreactive proteins from clinical samples following RNA and DNA isolation," *BioTechniques 35*:450-456, Informa Healthcare USA (Sep. 2003).

Bender, P.K. and Larson, T.J., "Chapter 23: PC/GENE: Sequence Comparisons and Homologies," in *Methods in Molecular Biology—Computer Analysis of Sequence Data: Part I 25*:283-288, Griffin, A.M. and Griffin, H.G., eds., Humana Press, Totowa, NJ (1994).

Bozon, V., et al., "Rescue of Intracellularly Trapped Lutropin Receptor Exodomain by Endodomain and Reconstitution of a Functional Membrane Receptor: Interaction between Exo- and Endodomains," *Protein Expr. Purif. 25*:114-123, Elsevier Science (2002).

Bruch, R.C., et al., "The Rat Ovarian Lutropin Receptor," *J. Biol. Chem. 261*:9450-9460, The American Society of Biological Chemists, Inc. (1986).

Bukovsky, A., et al., "Multiple luteinizing hormone receptor (LHR) protein variants, interspecies reactivity of anti-LHR mAb clone 3B5, subcellular localization of LHR in human placenta, pelvic floor and brain, and possible role for LHR in the development of abnormal pregnancy, pelvic floor disorders and Alzheimer's disease," *Reprod. Biol. Endocrinol. 1*:1-18, BioMed Central, Ltd. (Jun. 2003).

Carrillo, H. and Lipman, D., "The Multiple Sequence Alignment Problem in Biology," *Siam J. Appl. Math. 48*:1073-1082, Society for Industrial and Applied Mathematics (1988).

Casadesus, G., et al., "Evidence for the role of gonadotropin hormones in the development of Alzheimer disease," *Cell. Mol. Life Sci. 62*:293-298, Birkhäuser Verlag (Feb. 2005).

Chou, P.Y. and Fasman, G.D., "Conformational Parameters for Amino Acids in Helical, β-Sheet, and Random Coil Regions Calculated from Proteins," *Biochemistry 13*:211-222, The American Chemical Society (1974).

Cole, S.P.C., et al., "The EBV-Hybridoma Technique and its Application to Human Lung Cancer," in *Monoclonal Antibodies and Cancer Therapy*, Reisfeld, R.A. and Sell, S., eds., Alan R. Liss, Inc., New York, NY, pp. 77-96 (1985).

Davis, D.P., et al., "The Six N-linked Carbohydrates of the Lutropin/Choriogonadotropin Receptor Are Not Absolutely Required for Correct Folding, Cell Surface Expression, Hormone Binding, or Signal Transduction," *Mol. Endocrinol. 11*:550-562, The Endocrine Society (1997).

(Continued)

*Primary Examiner*—Jacob Cheu
(74) *Attorney, Agent, or Firm*—Seth D. Levy; Davis Wright Tremaine LLP

(57) ABSTRACT

The invention relates to a soluble luteinising hormone/chorionic gonadotropin receptor (LHCGR) protein and its use in diagnosing, treating and preventing conditions associated with over- and under-production of the said receptor, with over- and under-production of luteinising hormone, with over- and under-production of chorionic gonadotropin, with reproductive failure, with gonadal cancer and metastases, and Alzheimer's disease.

4 Claims, 10 Drawing Sheets

OTHER PUBLICATIONS

Devereux, J., et al., "A comprehensive set of sequence analysis programs for the VAX," *Nucl. Acids Res. 12*:387-395, IRL Press Limited (1984).

Dölz, R., "Chapter 7: GCG: Comparison of Sequences," in *Methods in Molecular Biology—Computer Analysis of Sequence Data: Part I 25*:65-82 , Griffin, A.M. And Griffin, H.G., eds., Humana Press, Totowa, NJ (1994).

Eblen, A., et al., "The Presence of Functional Luteinizing Hormone/Chorionic Gonadotropin Receptors in Human Sperm," J. *Clin. Endocrinol. Metab. 86*:2643-2648, The Endocrine Society (2001).

Eisenberg, D., et al., "The hydrophobic moment detects periodicity in protein hydrophobicity," *Proc. Natl. Acad. Sci. U.S.A. 81*:140-144, National Academy of Sciences (1984).

Engelman, D.M., et al., "Identifying Nonpolar Transbilayer Helices in Amino Acid Sequences of Membrane Proteins," *Ann. Rev. Biophys. Chem. 15*:321-353, Annual Reviews Inc. (1986).

Funaro, A., et al., "Functional, Structural, and Distribution Analysis of the Chorionic Gonadotropin Receptor Using Murine Monoclonal Antibodies," *J. Clin. Endocrinol. Metab. 88*:5537-5546, The Endocrine Society (Nov. 2003).

Henikoff, S. and Henikoff, J.G., "Amino acid substitution matrices from protein blocks," *Proc. Natl. Acad. Sci. U.S.A. 89*:10915-10919, National Academy of Sciences (1992).

Henikoff, S., "Chapter 4: Comparative Sequence Analysis: Finding Genes," in *Biocomputing: Informatics and Genome Projects*, Smith, D.W., ed., Academic Press, Inc., San Diego, CA, pp. 87-117 (1994).

Hipkin, R.W., et al., "Identification and Characterization of a Luteinizing Hormone/Chorionic Gonadotropin (LH/CG) Receptor Precursor in a Human Kidney Cell Line Stably Transfected with the Rat Luteal LH/CG Receptor Complementary DNA," *Mol. Endocrinol. 6*:2210-2218, The Endocrine Society (1992).

Jauniaux, E., et al., "HCG concentration and receptor gene expression in placental tissue from trisomy 18 and 21," *Mol. Hum. Reprod. 6*:5-10, European Society of Human Reproduction and Embryology (2000).

Kellokumpu, S. and Rajaniemi, H., "Involvement of Plasma Membrane Enzymes in the Proteolytic Cleavage of Luteinizing Hormone Receptor," *Endocrinology 116*:707-714, The Endocrine Society (1985).

Köhler, G. and Milstein, C., "Continuous cultures of fused cells secreting antibody of predefined specificity," *Nature 256*:495-497, Nature Publishing Group (1975).

Kolena, J., et al., "LH/hCG Receptor in Pig Follicular Fluid," *Endocrinol. Exp. 20*:339-348, Publishing House of The Slovak Academy of Sciences, Bratislava (1986).

Konishi, I., et al., "Increased Expression of LH/hCG Receptors in Endometrial Hyperplasia and Carcinoma in Anovulatory Women," *Gynecol. Oncol. 65*:273-280, Academic Press (1997).

Kozbor, D. and Roder, J.C., "The production of monoclonal antibodies from human lymphocytes," *Immunol. Today 4*:72-79, Elsevier Biomedical Press (1983).

Kremer, H., et al., "Male pseudohermaphroditism due to a homozygous missense mutation of the luteinizing hormone receptor gene," *Nat. Genet. 9*:160-164, Nature Publishing Group (1995).

Kyte, J. and Doolittle, R.F., "A Simple Method for Displaying the Hydropathic Character of a Protein," *J. Mol. Biol. 157*:105-132, Academic Press, Inc. (1982).

Lesk, A.M., ed., "Part III: Program Systems," in *Computational Molecular Biology. Sources and Methods for Sequence Analysis*, Oxford University Press, New York, NY, pp. 83-127 (1988).

Lesk, A.M., ed., "Part IV: The Technical Background," in *Computational Molecular Biology. Sources and Methods for Sequence Analysis Biology*, Oxford University Press, New York, NY, pp. 129-157 (1988).

Lewandowski, K., et al., "Free Leptin, Bound Leptin, and Soluble Leptin Receptor in Normal and Diabetic Pregnancies," *J. Clin. Endocrinol. Metab. 84*:300-306, The Endocrine Society (1999).

Lin, J., et al., "Lymphocytes from pregnant women express human chorionic gonadotropin/luteinizing hormone receptor gene," *Mol. Cell. Endocrinol. 111*:R13-R17, Elsevier Science Ireland Ltd. (1995).

Loosfelt, H., et al., "Cloning and Sequencing of Porcine LH-hCG Receptor cDNA: Variants Lacking Transmembrane Domain," *Science 245*:525-528, Association for the Advancement of Science (1989).

Maynard, S.E., et al., "Excess placental soluble fms-like tyrosine kinase 1 (sFlt1) may contribute to endothelial dysfunction, hypertension, and proteinuria and preeclampsia," *J. Clin. Invest. 111*:649-658, The American Society for Clinical Investigation (Mar. 2003).

McFarland, K.C., et al., "Lutropin-Choriogonadotropin Receptor: An Unusual Member of the G-Protein-Coupled Receptor Family," *Science 245*:494-499, Association for the Advancement of Science (1989).

Meduri, G., et al., "Luteinizing Hormone/Human Chorionic Gonadotropin Receptors in Breast Cancer," *Cancer Res. 57*:857-864, American Association for Cancer Research (1997).

Min, L. and Ascoli, M., "Effect of Activating and Inactivating Mutations on the Phosphorylation and Trafficking of the Human Lutropin/Choriogonadotropin Receptor," *Mol. Endocrinol. 14*:1797-1810, The Endocrine Society (2000).

Minegish, T., et al., "Cloning and Sequencing of Human LH/hCG Receptor cDNA," *Biochem. Biophys. Res. Commun. 172*:1049-1054, Academic Press, Inc. (1990).

Moncayo, H., et al., "Ovarian Failure and Autoimmunity: Detection of Autoantibodies Directed against Both the Unoccupied Luteinizing Hormone/Human Chorionic Gonadotropin Receptor and the Hormone-receptor Complex of Bovine Corpus Luteum," *J. Clin. Invest. 84*:1857-1865, The American Society for Clinical Investigation (1989).

Needleman, S.B. and Wunsch, C.D., "A General Method Applicable to the Search for Similarities in the Amino Acid Sequence of Two Proteins," *J. Mol. Biol. 48*:443-453, Academic Press (1970).

Nuamah, M.A., et al., "Free-to-Total Leptin Ratio in Maternal Plasma is Constant Throughout Human Pregnancy," *Endocrine J. 50*:421-428, The Japan Endocrine Society (Sep. 2003).

Osuga, Y., et al., "Derivation of Functional Antagonists Using N-Terminal Extracellular Domain of Gonadotropin and Thyrotropin Receptors," *Mol. Endocrinol. 11*:1659-1668, The Endocrine Society (1997).

Pabon, J.E., et al., "Human skin contains luteinizing hormone/chorionic gonadotropin receptors," *J. Clin. Endocrinol. Metab. 81*:2738-2741, The Endocrine Society (1996).

Pabon, J.E., et al., "Novel Presence of Luteinizing Hormone/Chorionic Gonadotropin Receptors in Human Adrenal Glands," *J. Clin. Endocrinol. Metab. 81*:2397-2400, The Endocrine Society (1996).

Pitard, V., et al., "The presence in human serum of a circulating soluble leukemia inhibitory factory receptor (sgp190) and its evolution during pregnancy," *Eur. Cytokine Netw. 9*:599-606, John Libbey Eurotext Ltd. (1998) as accessed at <http://www.john-libbey-eurotext.fr/en/print/e-docs/00/01/60/37/article.phtml>.

Rattan, S.I.S., et al., "Protein Synthesis, Posttranslational Modifications, and Aging," *Ann. N.Y. Acad. Sci. 663*:48-62, New York Academy of Sciences (1992).

Remy, J.-J., et al., "Purification and Structural Analysis of a Soluble Human Chorionogonadotropin Hormone-Receptor Complex," *J. Biol. Chem. 276*:1681-1687, The American Society for Biochemistry and Molecular Biology, Inc. (2001).

Rousseau-Merck, M.F., et al., "Localization of the human luteinizing hormone/choriogonadotropin receptor gene (LHCGR) to chromosome 2p21," *Cytogenet. Cell Genet. 54*:77-79, S. Karger AG, Basel (1990).

Rozell, T.G., et al., "Intracellular Retention of Mutant Gonadotropin Receptors Results in Loss of Hormone Binding Activity of the Follitropin Receptor but not the Lutropin/Choriogonadotropin Receptor," *Mol. Endocrinol. 9*:1727-1736, The Endocrine Society (1995).

Seifter, S. and Englard, S., "[47] Analysis for Protein Modifications and Nonprotein Cofactors," *Meth. Enzymol. 182*:626-646, Academic Press, Inc. (1990).

Singh, M., et al., "Decreased Expression of Functional Human Chorionic Gonadotropin/Luteinizing Hormone Receptor Gene in Human Uterine Leiomyomas," *Biol. Reprod. 53*:591-597, Society for the Study of Reproduction (1995).

States, D.J. and Boguski, M.S., "Chapter 3: Similarity and Homology," in *Sequence Analysis Primer*, Gribskov, M. and Devereux, J., eds., Stockton Press, New York, NY, pp. 89-157 (1991).
Tao, Y.-X., et al., "Expression of Luteinizing Hormone/Human Chorionic Gonadotropin Receptor Gene in Benign Prostatic Hyperplasia and in Prostate Carcinoma in Humans," *Biol. Reprod. 56*:67-72, Society for the Study of Reproduction (1997).
Tao, Y.-X., et al., "Seminal Vesicles are Novel Sites of Luteinizing Hormone/Human Chorionic Gonadotropin-Receptor Gene Expression," *J. Androl. 19*:343-347, American Society of Andrology (1998).
Thadhani, R., et al., "First Trimester Placental Growth Factor and Soluble Fms-Like Tyrosine Kinase 1 and Risk for Preeclampsia," *J. Clin. Endocrinol. Metab. 89*:770-775, The Endocrine Society (Feb. 2004).
Tsai-Morris, C.H., et al., "Intronic Nature of the Rat Luteinizing Hormone Receptor Gene Defines a Soluble Receptor Subspecies with Hormone Binding Activity," *J. Biol. Chem. 265*:19385-19388, The American Society for Biochemistry and Molecular Biology (1990).
Venencie, P.Y., et al., "Luteinizing hormone/human chorionic gonadotrophin receptors in various epidermal structures," *Brit. J. Dermatol. 141*:438-446, British Association of Dermatologists (1999).
Von Heijne, G., ed., "Chapter 6: Sequence Similarities, Homologies, and Alignments," in *Sequence Analysis in Molecular Biology: Treasure Trove or Trivial Pursuit*, Academic Press, San Diego, CA, pp. 123-139 (1987).
Vu Hai, M., et al., "Gonadotropin receptors," *Ann. Endocrinol. 60*:89-92, Masson Paris (1999).
Vuhai-Luuthi, M.T., et al., "Monoclonal Antibodies against Luteinizing Hormone Receptor. Immunochemical Characterization of the Receptor," *Endocrinology 127*:2090-2098, The Endocrine Society (1990).
Vuhai-Luuthi, M.T., et al., "Variant Forms of the Pig Lutropin/Choriogonadotropin Receptor," *Biochemistry 31*:8377-8383, American Chemical Society (1992).
Wimalasena, J. and Dufau, M.L., "Water-Soluble Gonadotropin Receptors of the Rat Ovary," *Endocrinology 110*:1004-1012, The Endocrine Society (1982).
Wimalasena, J., et al., "Soluble Luteinizing Hormone/Human Chorionic Gonadotropin Receptors of the Rat Ovary: Comparative Studies of Water- and Detergent-Soluble Receptors," *Endocrinology 113*:618-624, The Endocrine Society (1983).
Wold, F., "Posttranslational Protein Modifications: Perspective and Prospectives," in *Posttranslational Covalent Modifications of Proteins*, Johnson, B.C., ed., Academic Press, Inc., New York, NY, pp. 1-12 (1983).
Yoshida, K., et al., "Chapter 8: A Primer on Rapid Prototyping of Genomic Databases in Prolog," in *Biocomputing: Informatics and Genome Projects*, Smith, D.W., ed., Academic Press, Inc., San Diego, CA, pp. 233-248 (1994).
You, S., et al., "Three Different Turkey Luteinizing Hormone Receptor (tLH-R) Isoforms II: Characterization of Differentially Regulated tLH-R Messenger Ribonucleic Acid Isoforms in the Ovary," *Biol. Reprod. 62*:117-124, Society for the Study of Reproduction (2000).
Zou, J., et al., "Human Myometrial Chorionic Gonadotropin /Luteinizing Hormone Receptors in Preterm and Term Deliveries," *J. Clin. Endocrinol. Metab. 79*:907-911, The Endocrine Society (1994).
NCBI Entrez, Genbank Report, Accession No. NM_000233.3 (Entry Date Apr. 1999).
NCBI Entrez, Genbank Report, Accession No. NP_000224.2 (Entry Date Apr. 1999).
UniProtKB/Swiss-Prot Database, SwissProt ID P22888 (Entry Date Aug. 1991).
The HUGO Gene Nomenclature Database, Symbol Report on LHCGR (Last Update Apr. 2005).
Bowen, R.L., et al., "Luteinizing Hormone, a Reproductive Regulator That Modulates the Processing of Amyloid-β Precursor Protein and Amyloid-β Deposition," *J. Biol. Chem. 279*:20539-20545, American Society for Biochemistry and Molecular Biology (May 2004).
Eberhard, J., et al., "Risk factors for post-treatment hypogonadism in testicular cancer patients," *Eur. J. Endocrinol. 158*:561-570, BioScientifica Ltd. (Apr. 2008).
Garcia, J.M., et al., "Hypogonadism in Male Patients with Cancer," *Cancer 106*:2583-2591, American Cancer Society (Jun. 2006).
Rehman, H.U., and Masson, E.A., "Neuroendocrinology of ageing," *Age Ageing 30*:279-287, Oxford University Press.(2001).
Romerius, P., et al., "Hypogonadism Risk in Men Treated for Childhood Cancer," *J. Clin. Endocrinol. Metab. 94*:4180-4816, The Endocrine Society (Nov. 2009).
Webber, K.M., et al., "Estrogen Bows to a New Master: The Role of Gonadotropins in Alzheimer Pathogenesis," *Ann. N.Y. Acad. Sci. 1052*:201-209, New York Academy of Sciences (Jun. 2005).

* cited by examiner

Fig. 6: Diagnostic Tests for detecting sLHCGR in body fluids c. LHCGR Protein

1 MKQRFSALQLLKLLLLQPPLPRA 24

25 LREALCPEPCNCVPDGALRCPGPTAGLTRLS LAYLPVKVIPSQAFRG

LN[EVIKIEISQIESLERIEANAFDNLLNL_SEILIQNTENLRYIEPGAFINLPRLKYLSICNTGIRKFPDVTKVFS
                                                    210

SESNFILEICDNLHITTIPGNAFQGMNNESVTLKLYGNGFEEVQSHAFNGTLTLSLELKENVHLEKMQHNG
                                      229

AFRCGATGPKTLDESTICLQALPSYGLESIQRLIATSSYSLKKLFSRETFVNLLEAFLTYPSHCCAFRNLPTKE

QNFSHSISENESKQCESTVRKVSNETLYSSMLAESELSGWDYEYGFCLPKTPRCAPEPDAFNPCEDIMG

EC Domain

{MGLYLLLIASVDSCTKGQYYNH
YDFLRVLIWLINILAIMGNMTVLFVLLTSRYKLTVPRFLMCNLSFADFC}
                                           406
AIDWQTGSGCSTAGFFTVFASELSVYTLTVLTLERWHTITYAIHLDQKLRL RHAILIMLGG WLFSSLIAML

PLVGVSNYMAK VSICFPMDVE TTLSQVYILT ILILNVVAFFE ICACYIKIYFA VRNPELMA TNKDTKIAKK

MAILIFTDFTCMAPISFFAISAAAFKVPLIT VTNSKVLLVLF YPINSCANPFLY AIFT

TM Domain

KTFQRDFFLLLSKFGCC KRRAELYRRKDFSAYT SMCKNGFTGS NKPSQSTLKLSTLHCQGTALLDKTRYTEC
                                                                              701

IC Domain

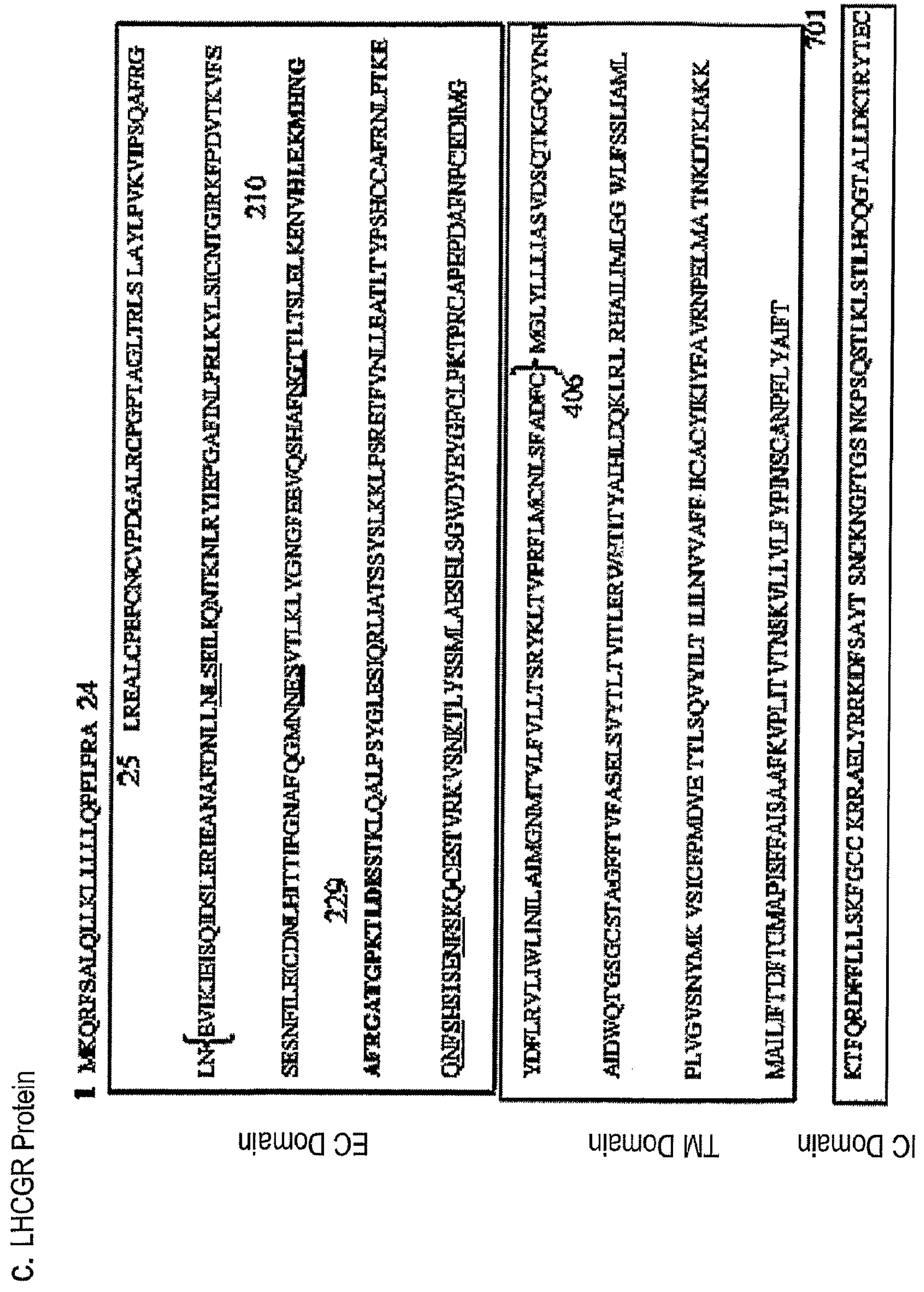

Fig. 8

DIAGNOSTIC AND THERAPEUTIC APPLICATIONS OF SOLUBLE LHCGR PROTEIN

The present invention is a U.S. National Phase filing under 35 U.S.C. §371 of PCT/GB2005/001473, filed Apr. 15, 2005, which claims priority to Great Britain Patent Application No. GB 0408449.7, filed Apr. 15, 2004, the disclosures of each of which are incorporated herein by reference in their entireties.

FIELD OF THE INVENTION

The present invention relates to a soluble luteinising hormone/chorionic gonadotropin receptor (LHCGR) protein and its use in diagnosis and therapy.

BACKGROUND OF THE INVENTION

Introduction

Human reproductive function is fundamentally regulated by hypothalamus-pituitary hormones (follicle stimulating hormone [FSH] and luteinising hormone [LH]) which act on ovary and testis to produce mature eggs and spermatozoa, respectively. These hormones are also vital for steroidogenesis resulting in the production of oestrogen and testosterone. The establishment and maintenance of human pregnancy requires an additional set of hormones—progesterone released from the corpus luteum and human chorionic gonadotropin (hCG) secreted from placenta. The receptors expressed on the surface of target cells for LH and hCG binding and signalling are identical and are therefore described as the LH/hCG receptor or LHCGR. The utilisation of a common receptor by two hormones with distinctly different physiological functions has profound implications in human reproductive failure, in a variety of pregnancy disorders, and in testicular, ovarian and breast cancers. The LHCGR gene encodes multiple mRNA species which are thought to be generated by alternative splicing. Thus, in addition to full-length functional LHCGR receptor protein, cells produce various isoforms including truncated soluble receptor (sLHCGR) which are not secreted.

The Reproductive Hormones

Reproductive hormones (LH, FSH and hCG) are collectively called gonadotropins because they stimulate gonads (testes in male and ovaries in female). They play specific and vital roles in human reproduction. For example, FSH stimulates sperm production by acting on Sertoli cells of the testis in males, whereas in females it stimulates maturation of the ovarian follicles. In both sexes, LH induces the production and secretion of sex steroids from gonads. In males, LH binds to its receptor on Leydig cells and facilitates the production and secretion of testosterone. In the ovary, LH binds to thecal cells and stimulates the production of testosterone which is converted to oestrogen by neighbouring granulosa cells. Additionally, in females, a surge of LH facilitates the ovulation of mature follicles. Following ovulation, the remaining cells of the follicle are luteinised by LH and produce progesterone and oestradiol which are necessary for implantation of the embryo. Of the three gonadotropins, LH and FSH are secreted by the anterior pituitary, a gland situated in the brain, while hCG is almost exclusively released by the placenta (FIG. 1). The major function of hCG in early pregnancy is to sustain the newly formed corpus luteum on the surface of the ovary, which produces progesterone in early pregnancy.

Two Hormones—One Receptor: LH and hCG use a Common Receptor

The hormone hCG functions by binding to a specific receptor expressed on the surface of the cell. Because LH and hCG use a common receptor that is encoded by a single copy ~70 kb LHCGR gene, located at human chromosome 2p21,[1-3] it is often referred to as the LH/hCG receptor (LHCGR). Structurally, this receptor is very similar to thyroid and follicle stimulating hormone receptors. LHCGR has 11 exons and codes for multiple alternatively spliced species (at least 6) of mRNA (FIG. 8). Transcription to form these mRNAs is initiated at multiple sites spanning a region more than a kilobase upstream of the first exon.[1,2]

On the basis of structure and topology, LHCGR is a member of the rhodopsin/β-adrenergic receptor superfamily of G protein-coupled receptors. Agonist binding to LHCGR allows dissociation of membrane-bound cognate G proteins that regulate phospholipase C, adenylyl cyclase and ion channels which in turn control cellular inositol phosphates, cAMP, $Ca^{+2}$ and other secondary messengers.[4]

The largest receptor encoded by the LHCGR gene is a 677-amino acid protein that has three distinct domains; an unusually large (340 residues) N-terminal extracellular domain which binds hCG, a serpentine transmembrane region containing seven repeats connected by three extra- and intracellular loops, and a C-terminal tail (FIG. 8). The predicted relative molecular mass of this protein is ~75K or higher depending upon the level of glycosylation.[4] Moreover, alternatively spliced mRNAs produce several truncated proteins which have the ligand binding capacity but are ineffective in transducing signals.[5-7] In addition to testis, ovary and placenta, various isoforms of LHCGR are expressed in uterine myometrium, vascular endothelial and smooth muscle cells, brain, lymphocytes, human sperm, macrophages and in various foetal tissues.[8]-23

Mammalian cells transfected with human LHCGR cDNA produce several distinct species of proteins ranging from $M_r$ 45-48K to 165-200K in denaturing polyacrylamide gels.[4, 22-29] The specific function of all of these receptor proteins remains to be established. However, the accessibility of the $M_r$ 85-95K species to surface biotinylation, protease and glycosidase (neuraminidase), suggests that they have ligand binding and signal transduction capabilities.[30] On the other hand, the $M_r$ 65-75K proteins contain high-mannose type side chains which are susceptible to endoglycosidase H (Endo H), suggesting that these are immature intracellular proteins.[6, 31] Recent studies suggest that the $M_r$ 165-200K proteins are LHCGR dimers.[22] Interestingly, smaller LHCGR species ($M_r$ 45-51K) are detected in human tissues or in cells transfected with mutant rat lhcgr where glycosylation sites at the extracellular domain are mutated.[22-29, 32-35] These smaller species might represent soluble LHCGR receptor and are most likely to be the translation products of truncated LHCGR mRNAs.[4-7, 22, 27-29, 32-35]

Clinical Importance of LHCGR

Human Infertility and Ovarian Hyperstimulation

One of the important aspects of the female reproductive cycle is that ovulation is controlled by a pulsatile secretion of LH (also known as an LH surge) which varies depending upon the individual. This variability can be clinically controlled on the basis of our knowledge of the feed-back regulation of LH/FSH secretion. Briefly, the LH/FSH production in pituitary cells (known as gonadotrophs) is stimulated by another hormone released from the hypothalamus region of the brain called gonadotropin releasing hormone (GnRH). However, GnRH production is inhibited by sex steroids (oestrogen and testosterone). Based on this knowledge, two types of drugs are used by clinicians to induce ovarian hyperstimulation: a) drugs that mimic GnRH functions (agonists) and b) drugs that inhibit GnRH functions (antagonists) (FIG. 1).

In a normal physiological cycle, the ovary is under the control of FSH and LH released from the pituitary. During ovarian hyperstimulation treatment, this control is temporarily eliminated, while at the same time ovarian functions are artificially regulated by exogenously injected FSH and LH. Buserelin and nafarelin are analogues of GnRH. Given as a single dose, these analogues stimulate the release of LH and FSH from the pituitary with consequent increase of ovarian and testicular steroidogenesis. However, repeated dosing of these analogues has the opposite effect. For instance, when administered twice daily, LH/FSH secretion from the pituitary subsides, leading to the suppression of ovarian function. Cetrorelix is a synthetic hormone that blocks GnRH function and therefore prevents the production and release of LH/FSH from the pituitary. One of the advantages of cetrorelix is that it prevents premature ovulation (egg release) during ovarian hyperstimulation. GnRH agonists or antagonists, together with exogenously administered gonadotropins are therefore used in ovarian hyperstimulation.

Human Pregnancy

Compared with other mammals, human pregnancy is unique in that there is extensive invasion of the uterine myometrium by haemochorial placenta. The chorionic villi represent the structural and functional units of placenta. Each villus has a central mesenchymal core surrounded by a layer of multinucleated syncytotrophoblasts. In addition to transporting nutrients from the maternal blood, the syncytotrophoblasts produce a variety of steroids, hormones and growth factors. The key reproductive hormone in regulating mammalian pregnancy is hCG which is member of a family of glycoprotein hormones including LH, FSH and thyroid stimulating hormone. Each member of this family functions by forming a non-covalent heterodimer from two subunits, $\alpha$ and $\beta$. The $\alpha$ subunit is synthesized in excess and is common to all members of this family, whereas the $\beta$ subunit, which recognizes the cognate receptor, is specific for each hormone. In humans, the common $\alpha$ subunit is encoded by a single gene on chromosome 6 while there are several copies of the gene encoding hCG$\beta$ located on chromosome 19.

In human placenta hCG is primarily produced by syncytotrophoblasts and to a lesser extent by extravillous cytotrophoblasts. One of the earliest endocrine roles of hCG is to sustain the corpus luteum to produce sufficient progesterone in order to establish the pregnancy. In addition, hCG facilitates trophoblast differentiation and remodelling of the uterine epithelium (decidualisation) and endometrium for implantation. By acting on vascular smooth muscle and endothelial cells hCG also plays a role in angiogenesis, and facilitates the invasion of maternal spiral arterioles. Free hCG$\beta$ begins to appear in the maternal circulation at around 6-8 weeks of pregnancy, reaches its peak at 11-13 wks and its serum concentration is reduced at the later stages of the pregnancy. Interestingly, high serum hCG$\beta$ levels at the later stages of pregnancy are often associated with pre-eclampsia, intra-uterine growth restriction and Down's syndrome.

Down's Syndrome and Other Genetically Compromised Pregnancies

About 50% of human pregnancies miscarry and one in five pregnancies fail to proceed after the first term due to chromosomal abnormalities. Between 10 and 30% of fertilised human eggs are aneuploid (trisomy and monosomy). The incidence of aneuploidy in human pregnancies is unusually high (1-2%) compared with other mammals. Monosomies and trisomies together account for 35% of clinically detected spontaneous abortions (6-20 wks of gestation), stillbirth (4%) and most importantly, are the leading cause of developmental disability and mental retardation in those surviving such pregnancies. Of all genetically compromised pregnancies, Down's syndrome (trisomy 21; T21) is the most frequent (1/700 live births). Although, Edward's (trisomy 18; T18) and Pautau's (trisomy 13; T13) syndromes are considered relatively rare pregnancy disorders (1/1800 births), they are as common as cystic fibrosis and more common than muscular dystrophy and neurofibromatosis. About 30-35% of foetuses with Down's syndrome fail to reach term and most (85-88%) with complete Edward's or Pautau's syndromes either do not survive pregnancy or fail to progress beyond six months post-naturally.

Pre-Eclampsia

Pre-eclampsia affects 5-7% of pregnant women world-wide. It is the major cause of maternal mortality (80%) in developing nations and in the recent years, the peri-natal mortality in developed countries has increased by five-fold. The disease is clinically recognised by hypertension at mid-late gestation, proteinurea and intra-uterine growth restriction. These clinical features are often linked to superficial implantation of the foetus, inadequate placental perfusion and systemic vascular endothelial dysfunction.

Prior Studies of the LHCGR Receptor

Following the isolation of cDNA clones for LHCGR,[1, 2] a tremendous amount of work has been published on the characterisation[4-7] and chromosomal localisation of the LHCGR gene,[3] on alternatively spliced mRNA species produced in tissues[5-7] and on the identification of various isoforms of LHCGR proteins[5, 6, 10-22].

The mature functional LHCGR protein has an unusually large N-terminal domain consisting of ~340 amino acids and is called the extracellular domain. Several laboratories have been successful in expressing the recombinant form of this domain in animal cell culture and the truncated version of LHCGR has been shown to be released into the cell culture media[5, 23, 27, 32-34]. Drs. Aaron Hsueh and Brian Kobilka (Stanford University, California) have patented the application of the method of producing a recombinant form of the soluble LHCGR for therapeutic purposes (U.S. Patent described as "Soluble 7-Transmembrane Domain G-Protein Coupled Receptor Compositions and Methods", licensed to Procyon Biopharma, Montreal, 2001)

Hormone and cytokine receptors are integral parts of the cell membrane. However, as described in this application, the release of truncated or modified isoforms of some receptors from cell membranes and their presence in body fluids, is not unprecedented. Soluble, secreted receptors are generated either by proteolytic cleavage of the membrane-bound receptor or by translation of alternatively spliced mRNAs. For example, tumour necrosis factor $\alpha$ (TNF a U.S. Pat. No. 6,663,865; Tumour necrosis factor antagonists and their use in endometriosis, Dec. 16, 2003 and ref. 39), leukaemia inhibitory factor[40] liptin[41, 42] receptor, and soluble vascular endothelial growth factor receptor (sFlt-1) are detected in the serum of pregnant women.[37, 38] The serum level of sFlt-1 rises significantly in pre-eclampsia (PE) compared to that of age-matched control pregnancies. The invention that sFlt-1 could serve as biomarker in pregnant serum and its application in diagnosis of PE has been patented by Dr. Richard Levine (Beth Israel Deaconess Medical Center, Boston, Mass., USA) who has licensed the patent to Scios Inc., an affiliate of Johnson & Johnson. The major disadvantages of this system are that serum sFlt-1 is not a universal marker for PE and that the level of sFlt-1 in serum only shows an increase in late pregnancy.

BRIEF DESCRIPTION OF THE INVENTION

While the published reports suggest that all LHCGR protein isoforms are trapped inside the cell, 4, 22, 25 the present invention underscores that at least one isoform ($M_r$, 48-50K) is released from the cell and can be detected in the human serum and follicular fluid. It should be noted, however, that work carried out about 15 years ago suggested that soluble LH receptor may be present in pig, rabbit and bovine, but not sheep follicular fluid[8]. Corresponding studies on human material have never been reported.

The soluble LHCGR protein, the subject of the present invention, has an estimated molecular weight (M) of about 50K, an estimated length of about 450-470 amino acid residues, and appears to contain substantially the entire N-terminal extracellular domain of the full length (mature) receptor.

We have now discovered an LHCGR isoform that is released from the tissues into the bloodstream of pregnant women and is also found in the follicular fluid of those undergoing ovarian hyperstimulation in IVF clinics. Because the soluble receptor is capable of binding both LH and hCG (LH/CG), it can therefore incapacitate these ligand hormones before they can interact with the membrane bound cognate receptor. The conventional measurement of serum LH/hCG concentrations for diagnosis of various clinical conditions is therefore insufficient to establish receptor-bound versus free hormone levels. The ability to accurately measure active LH/hCG in body fluids has multiple diagnostic and therapeutic applications in clinical reproductive medicine.

In the following description, the soluble LHCGR protein of the present invention will sometimes be referred to as sLHCGR or $LHCGR_s$. The mature (full length) LHCGR receptor known in the prior art will sometimes be referred to as $LHCGR_m$.

According to one aspect of the present invention, there is provided an isolated soluble LHCGR polypeptide comprising the amino acid sequence of SEQ. ID. NO. 1, or variants, analogues or functional fragments thereof.

According to a second aspect of the present invention, there is provided a soluble LHCGR polypeptide of human origin comprising the amino acid sequence of SEQ. ID. NO. 1, or variants, analogues or functional fragments thereof.

The polypeptide is preferably naturally occurring (i.e. not obtained by chemical synthesis or by expression of a recombinant or other manipulated gene).

The polypeptide may be of primate, e.g. human, origin, particularly from human ovarian follicular fluid, serum (blood), urine or semen. The polypeptide may be of equine or bovine origin, particularly from equine or bovine ovarian follicular fluid, serum (blood), urine or semen.

In one particular embodiment of the invention, the soluble LHCGR polypeptide may be of mammalian body fluid (e.g. primate (e.g. human), equine or bovine) origin other than ovarian follicular fluid, e.g. serum (blood), urine or semen.

According to a third aspect of the present invention, therefore, there is provided a soluble LHCGR polypeptide of mammalian body fluid origin other than ovarian follicular fluid, comprising the amino acid sequence of SEQ. ID. NO. 1, or variants, analogues or functional fragments thereof.

The soluble LHCGR polypeptide or variant, analogue or fragment thereof according to the present invention may suitably consist essentially of the said amino acid sequence of SEQ. ID. NO. 1.

A soluble LHCGR polypeptide consisting essentially of the said amino acid sequence of SEQ. ID. NO. 1, or variants or analogues thereof may have a relative molecular mass of approximately 48-50K as determined according to its electrophoretic migration through denaturing polyacrylamide gels using proteins of known molecular weight as marker proteins. It will be noted that glycosylation may in some cases cause the relative molecular mass of the protein to vary slightly outside the above approximate molecular mass range.

The soluble LHCGR polypeptide or variant, analogue or fragment thereof according to the present invention may suitably be present in isolated form.

The soluble LHCGR polypeptide or variant, analogue or fragment thereof according to the present invention may alternatively be present in the form of a solution in blood, blood serum, urine or semen removed from the human or non-human animal body.

The soluble LHCGR polypeptide or variant, analogue or fragment thereof according to the present invention may suitably be present in the form of a complex with a hormone to which it binds, for example a hormone selected from CG (e.g. hCG) and LH. Such a receptor/hormone complex may further comprise one or more species which bind to the receptor and/or to the hormone, such as one or more antibody thereto.

In other aspects, the present invention provides a polynucleotide capable of encoding the soluble LHCGR polypeptide according to the present invention (including variants, analogues or fragments thereof), a polynucleotide capable of hybridising thereto under stringent conditions, an expression vector comprising such a polynucleotide sequence, a host cell comprising such an expression vector, an antibody or other inhibitor of the polypeptide, an anti-idiotypic antibody thereto, compositions comprising any of the above, the soluble LHCGR polypeptide or variant, analogue or fragment thereof for use as a medicament or diagnostic agent, the above-mentioned polynucleotide for use as a medicament or diagnostic agent, the above-mentioned antibody or other inhibitor or anti-idiotypic antibody for use as a medicament or diagnostic agent, and uses of any of the above in diagnosis and therapy.

Such a polynucleotide may for example have the nucleic acid sequence shown in SEQ. ID. NO. 2.

The polynucleotide according to the present invention may for example be present in isolated form.

For example, a use of the material of the present invention may be a method of diagnosing a condition selected from human infertility conditions, ovarian hyperstimulation, egg maturation disorders, polycystic ovarian syndrome, miscarriage, Down's syndrome and other trisomic pregnancy conditions, molar pregnancy, pre-eclampsia, intra-uterine growth restriction, testicular cancer and ovarian cancer in a subject, or for use in the diagnosis of susceptibility thereto, which comprises assaying a sample of body fluid obtained from the subject for the presence of the soluble polypeptide or for the presence of a hormone capable of binding thereto, or for the presence of a complex of said polypeptide and said hormone, and making the said diagnosis having regard to the assay result.

Another use of the material of the present invention may be a method of treating or preventing a pregnancy condition characterised by high total but low free LH or hCG serum or urine concentrations in a subject in need thereof, which comprises administering to the subject an effective amount of an antagonist or specific binding partner of the soluble polypeptide (including variants, analogues or fragments thereof).

The antagonist or specific binding partner may be an antibody or other inhibitor of the said polypeptide (including variants, analogues or fragments thereof).

The present invention further provides a pharmaceutical composition comprising the polypeptide and a physiologically acceptable diluent, excipient or carrier.

The present invention also provides a pharmaceutical composition comprising the polynucleotide and a physiologically acceptable diluent, excipient or carrier.

The present invention also provides an expression vector comprising a polynucleotide sequence capable of encoding the soluble LHCGR polypeptide, and a host cell comprising the said expression vector.

The present invention further provides the use of the polypeptide or a polynucleotide capable of encoding the same as an immunogen to produce an antibody immunospecific for such polypeptides or polynucleotides respectively or the use of an antibody specific to the said polypeptide or polynucleotide to produce an anti-idiotypic antibody thereto.

The present invention further provides an antibody produced against a soluble LHCGR polypeptide consisting essentially of the amino acid sequence of SEQ. ID. No. 1 or a variant, analogue or functional fragment thereof, or an anti-idiotypic antibody thereto.

The present invention further provides an antibody produced against a polynucleotide capable of encoding a soluble LHCGR polypeptide consisting essentially of the amino acid sequence of SEQ. ID. No. 1 or a variant, analogue or functional fragment thereof, or an anti-idiotypic antibody thereto.

The antibody is suitably specific and is preferably monoclonal. The antibody may preferably be in isolated form.

These and further aspects and embodiments of the present invention are described below and are defined by the appended claims.

DETAILED DESCRIPTION OF THE INVENTION

Terminology

The term "isolated" as used herein means altered from its natural state, i.e., if it occurs in nature, it has been changed or removed from its original environment, or both. For example, a polynucleotide or a polypeptide naturally present in a living organism is not "isolated", but the same polynucleotide or polypeptide separated from the coexisting materials of its natural state is "isolated", as the term is used herein. Moreover, a polynucleotide or polypeptide that is introduced into an organism by transformation, genetic manipulation or by another recombinant method is "isolated" even if it is still present in said organism, which organism can be living or non-living. The term "isolated" in the context of the present invention refers particularly but not exclusively to polynucleotide material which is unassociated with a chromosome and polypeptide material which is unassociated with a cell.

The term "soluble" as used herein in relation to the polypeptides of the invention means capable of dissolving under normal physiological conditions in body fluids such as one or more of serum, urine, seminal plasma and follicular fluid, without substantial binding to body tissue.

The term "variant(s)" as used herein refers particularly to a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and/or truncations in the polypeptide encoded by the reference sequence, as discussed below. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more substitutions, additions, and/or deletions in any combination. A substituted or inserted amino acid residue may or may not be one encoded by the genetic code. The present invention also includes variants of each of the polypeptides of the invention, that is polypeptides that vary from the references by conservative amino acid substitutions, whereby a residue is substituted by another with like characteristics. Typical conservative amino acid substitutions are among Ala, Val, Leu and Ile; among Ser and Thr; among the acidic residues, Asp and Glu; among Asn and Gln; and among the basic residues Lys and Arg; or aromatic residues Phe and Tyr. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

Such conservative variations can further include the following:

| Original Residue | Variation |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of variations selected can be based on the analysis of the frequencies of amino acid variations between homologous proteins of different species developed by Schulz et al. (*Principles of Protein Structure*, Springer-Verlag, 1978), on the analyses of structure-forming potentials developed by Chou and Fasman (*Biochemistry* 13:211, 1974 and *Adv. Enzymol.,* 47:45-149, 1978), and on the analysis of hydrophobicity patterns in proteins developed by Eisenberg et al. (*Proc. Natl. Acad. Sci. USA* 81:140-144, 1984), Kyte & Doolittle (*J. Molec. Biol.* 157: 105-132, 1981), and Goldman et al. (*Ann. Rev. Biophys. Chem.* 15:321-353, 1986). Particularly preferred are variants in which several, e.g., 5-10, 1-5, 1-3, 1-2 or 1 amino acids are substituted, deleted, or added in any combination. A variant of a polynucleotide or polypeptide may be naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to a person skilled in the art.

Variants which are known, from work done on the full-length mature LHCGR protein, to occur naturally in the extracellular domain of that protein will be expected to occur naturally also in the soluble LHCGR protein of the present invention. In particular, a number of polymorphisms have been observed in exon 1 (insertion of amino acids IQ at residue 18 being most common) and in exons 8, 11) and 11. In addition, a relatively large number of activating mutations which are primarily restricted to exon 11 (for example, A373V, M398T, L457R, I542L, D564G, A568V, M571I, A572V, I575L, T577I, D578G/Y/H/E, C581R) and inactivating mutations (for example, insertion at residue 18-LLKLLLLLQLQ, deletions in exons 8, 10) and single nucleotide mutations at C131R, F194V, C343S, E354K, W491X, C543R, C545X, R554X, A593P, S616Y and I625K have been reported.

The term "analogue(s)" as used herein refers in particular to peptidomimetics, such as those formed using small non-protein molecules having corresponding ligand binding properties to the polypeptide. The anti-idiotypic antibodies mentioned below, which may be raised to antibodies of the polypeptide, can be considered as a further analogue of the polypeptide.

The term "functional fragments" as used herein refers to shortened portions of the polypeptide sequence which retain effective function in comparison with the full length polypeptide. Such functional fragments can readily be obtained and identified by persons skilled in the art using readily available protein formation or digestion technology and assay systems. Such fragments will generally contain a number of amino acids corresponding to at least about 90% of the total number of amino acids of SEQ. ID. NO. 1, for example at least about 95%, for example at least about 97%, for example at least about 98% of the total number of amino acids of SEQ. ID. NO. 1.

The term "polynucleotide(s)" as used herein generally refers to any polyribonucleotide or polydeoxyribonucleotide, which may be unmodified RNA or DNA or modified RNA or DNA. Polynucleotide(s) include, without limitation, single- and double-stranded DNA, DNA that is a mixture of single- and double-stranded regions or single- and triple-stranded regions, single- and double-stranded RNA, and RNA that is a mixture of single- and double-stranded regions, hybrid molecules comprising DNA and RNA that can be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as the term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as used herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides, often referred to as oligonucleotide(s).

The term "polypeptide(s)" as used herein refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides can contain amino acids other than the 20 gene encoded amino acids. "Polypeptide(s)" include those modified either by natural processes, such as processing and other post-translational modifications, but also by chemical modification techniques. Such modifications are well described in research literature, and are well known to those skilled in the art. It will be appreciated that the same type of modification can be present at the same or varying degrees at several sites in a given polypeptide. Also, a given polypeptide can contain many types of modification. Modification can occur anywhere in a polypeptide, including the peptide backbone, the amino acid side-chains, and the amino or carboxyl termini. Modifications include, for example, acetylation, acylation, ADP-ribosylation, amidation, covalent attachment of Ravin, covalent attachment of a heme moiety, covalent attachment of a nucleotide or a nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, transfer-RNA mediated addition of amino acids to proteins, such as arginylation, and ubiquitination. See, for instance, *PROTEINS—STRUCTURE AND MOLECULAR PROPERTIES,* 2nd Ed., T.E. Creighton, W.H. Freeman and Company, New York (1993) and Wold, F., Posttranslational Protein Modifications: Perspectives and Prospects. pgs 1-12 in *POSTTRANSLATIONAL COVALENT MODIFICATION OF PROTEINS*, B. C. Johnson. Ed., Academic Press, New York (1983); Seifter et al., Meth. Enzymol. 182:626-646 (1990) and Rattan et al., *Protein Synthesis: post-translational Modifications and Aging*, Ann. N.Y. Acad. Sci. 663: 48-62 (1992). Polypeptides can be branched, or cyclic, with or without branching. Cyclic, branched and non-branched polypeptides can result from post-translational natural processes and can be made by entirely synthetic methods as well.

The term "polypeptide" used herein therefore includes glycosylated forms of the amino acid sequence as defined. For example, it is known that the extracellular domain (ECD) of the mature human LHCGR contains six highly conserved N-linked glycosylation sites (see FIG. 8*b* below, the sites there underlined). It is believed that the six N-linked carbohydrates of the mature LHCG receptor are not absolutely required for correct folding, cell surface expression, hormone binding, or signal transduction. Since the contribution of a single oligosaccharide chain linked to each N-linked glycosylation site is approximately 2K ($M_r$), the maximum estimated contribution by six side-chain oligosaccharide to a 50K-60K sLHCGR would be 10K (Davis D P, Rozell T G, Liu X, Segaloff D L, Mol. Endocrinol. 11: 550-62, 1997). Therefore, the total number of amino acid residues in a 50K-60K sLHCGR is estimated to be 363 to 436 (average $M_r$ of amino acid is 110).

Preferably, at least a portion of the polypeptide comprises at least 66% identity to the sequence shown in SEQ. ID No. More preferably, at least a portion of the polypeptide comprises at least 83% identity to the sequence shown in SEQ. ID No.1.

The term "identity" as used herein is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988*; Biocomputing: Informatics and genome Projects*, Smith, D. W., ed., Academic Press, New York. 1993*; Computer Analysis of sequence Data*, Part I, Griffin, A. M., and Griffin, H. G., eds., Humana Press. New jersey, 1994*; sequence Analysis in Molecular Biology*, von Heinje, G., Academic Press, 1987; and *sequence Analysis Primer*, Gribskov, M. and Devereux, J., eds., M Stockton Press, New York, 1991; and Carillo, H., and Lipman, D., SIAM J. *Applied Math.,* 48:1073 (1998). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J Molec. Biol.* 215: 403-410 (1990). The BLAST X program is publicly available from NCBI and other sources (BLAST Manual, Altschul, S., et al., NCBI NLM NUR Bethesda, Md. 20894; Altschul, S., et al., *J. Mol. Biol.* 215: 403-410 (1990).

Parameters for polypeptide sequence comparison include the following:

Algorithm: Needleman and Wunsch, J. Mol. Biol. 48:443-453 (1970) Comparison matrix: BLOSSUM62 from Henikoff & Henikoff, Proc. Natl. Acad. Sci. USA. 89:10915-10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparison (along with no penalty for end gaps). In all cases where a computer program that does not necessarily give the maximized alignment discussed above is used to determine a measure of identity, the default parameters are preferred. Parameters for polynucleotide comparison include the following:

Algorithm; Needleman and Wunsch, J. Mol. Biol. 48: 443-453 (1970)

Comparison matrix: matches=+10, mismatch=0

Gap Penalty: 50

Gap Length Penalty: 3

Where the sequence shown in SEQ ID NO. 1 occurs in a larger soluble polypeptide as part of a longer sequence, the total length of said longer sequence is preferably less than about 510 amino acids (aa), for example less than about 500 aa, for example less than about 490 aa, for example less than about 480 aa, for example less than about 470 aa. The additional amino acids may be linked at the N-terminal end of the sequence shown in SEQ ID NO. 1, at the C-terminal end of the sequence shown in SEQ ID NO. 1, or at both the N-terminal and C-terminal ends of the sequence shown in SEQ ID NO. 1.

Where the sequence shown in SEQ ID NO. 1 occurs in a larger soluble polypeptide as part of a longer sequence, the length of the sequence of the said additional amino acids, or—if at both the N- and C-terminal ends of the sequence shown in SEQ ID NO. 1—each of such sequences of additional amino acids, is preferably less than about 40 aa, for example less than about 20 aa, for example less than about 10 aa, for example less than about 5 aa, for example about 2 aa.

Where the sequence shown in SEQ ID NO. 1 occurs in a larger polypeptide as part of a longer sequence, the functionality of the sequence shown in SEQ ID NO. 1 is substantially maintained in the larger polypeptide.

As used herein the term "stringent conditions" means hybridisation occurring only if there is at least 83% identity between the sequences. A specific example of stringent hybridisation conditions is overnight incubation at 42° C. in a solution comprising: 50% formamide. 5×SSC (150 mM NaCl, 15 mM trisodium citrate), 50 mM sodium phosphate (pH 7.6), 5×Denhardt's solution, 10% dextran sulphate, and 20 micrograms/ml of denatured, sheared salmon sperm DNA, followed by washing the hybridisation support in 0.1×SSC at about 65° C. Hybridisation and wash conditions are well known and exemplified in Sambrook, et al., Molecular Cloning: A Laboratory Manual, Third Edition, Cold Spring Harbour, N.Y., (1989), particularly Chapter II therein. Solution hybridisation can also be used with the polynucleotide sequences provided by the invention.

Preparation of the Polypeptides

Naturally occurring polypeptides according to the present invention may conveniently be isolated from suitable natural sources, particularly mammalian body fluids and tissues such as placental tissue, serum (blood), urine, seminal plasma and follicular fluid. Suitable mammalian species include primates (e.g. humans), horses and cattle.

Such polypeptides can be recovered and purified from the body fluids by well-known methods, including ammonium sulphate or ethanol precipitation, extraction such as acid extraction, anion or cation exchange chromatography, gel filtration, phosphocellulose chromatography, hydrophobic interaction chromatography, affinity chromatography, hydroxylapatite chromatography, lectin chromatography, preparative electrophoresis, FPLC (Pharmacia, Uppsala, Sweden), HPLC (e.g., using gel filtration, reverse-phase or mildly hydrophobic columns). Most preferably, affinity chromatography is employed for purification. Well known techniques for refolding proteins can be employed to regenerate an active conformation after denaturation of the polypeptide during isolation and/or purification.

Alternatively, the polypeptides according to the present invention may be produced recombinantly.

For recombinant production of the polypeptides of the invention, host cells can be genetically engineered to incorporate expression systems or portions thereof or polynucleotides of the invention. Introduction of a polynucleotide into a host cell may be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL,* 2nd Ed., Cold Spring Harbour Laboratory Press, Cold Spring Harbour. N.Y. (1989), such as, calcium phosphate transfection, DEAE-dextran mediated transfection, transfection, microinjection, cationic lipid-mediated transfection, electroporation, transduction, scrape loading, ballistic introduction and infection.

Representative examples of appropriate hosts include bacterial cells, such as streptococci, staphylococci, enterococci *E. coli, streptomyces*, cyanobacteria, *Bacillus subtilis*; fungal cells, such as yeast, *Kluveromyces, Saccharomyces*, a basidiomycete, *Candida albicans* and *Aspergillus*; insect cells such as *Drosophila* S2 and *Spodoptera* Sf9; animal cells such as CHO, COS, HeLa, C127, 3T3, BHK, 293, CV-1 and Bowes melanoma cells; and plant cells.

A great variety of expression systems can be used to produce the polypeptides of the invention. Such vectors include, among others, chromosomal-, episomal- and viral-derived vectors, for example, vectors derived from plasmids, from bacteriophage, from transposons, from yeast episomes, from insertion elements, from yeast chromosomal elements, from viruses such as baculoviruses, papova viruses, such as SV40, vaccinia viruses, adenoviruses, adeno-associated viruses, avipox (e.g. fowl pox) viruses, suipox viruses, capripox viruses, pseudorabies viruses, picornaviruses and retroviruses, and vectors derived from combinations thereof, such as those derived from plasmid and bacteriophage genetic elements, such as cosmids and phagemids. The expression system constructs can contain control regions that regulate as well as engender expression. Generally, any system or vector suitable to maintain, propagate or express polynucleotides or to express a polypeptide in a host can be used for expression in this regard. The appropriate DNA sequence can be inserted into the expression system by any of a variety of well-known and routine techniques, such as, for example, those set forth in Sambrook, et al., *MOLECULAR CLONING: A LABORATORY MANUAL*, (supra).

For assisted secretion of a translated protein into the lumen of the endoplasmic reticulum, into the periplasmic space or into the extracellular environment, appropriate secretion signals may be incorporated into the expressed polypeptide. These signals can be endogenous to the polypeptide or they can be heterologous signals.

Polypeptides of the invention can be recovered and purified from recombinant cell cultures by well-known methods, including ammonium sulphate or ethanol precipitation, extraction such as acid extraction, anion or cation exchange chromatography, gel filtration, phosphocellulose chromatography, hydrophobic interaction chromatography, affinity chromatography, hydroxylapatite chromatography, lectin chromatography, preparative electrophoresis, FPLC (Pharmacia, Uppsala, Sweden), HPLC (e.g., using gel filtration, reverse-phase or mildly hydrophobic columns). Most preferably, affinity chromatography is employed for purification. Well known techniques for refolding proteins can be employed to regenerate an active conformation after denaturation of the polypeptide during isolation and/or purification.

After production, the polypeptides can be assayed for activity using a range of standard protein activity assays. Such assays will be well known to those skilled in the art, and further discussion is not necessary here.

Preparation of the Polynucleotides

The polynucleotides according to the present invention may be prepared from suitable naturally occurring or synthesised precursor material by any of the well known techniques for assembling and/or modifying and/or isolating polynucleotide material.

For example, a polynucleotide according to the present invention may be prepared from genomic DNA of the LHCGR gene or a portion thereof.

Preparation of the Antibodies or Other Inhibitors

A polypeptide, or polynucleotide comprising a nucleotide sequence, according to the present invention or variants thereof, or cells expressing the same can be used as immunogens to produce antibodies immunospecific for such polypeptides or nucleotide sequences respectively.

Such antibodies and other inhibitors of the polypeptides or nucleotide sequences constitute further features of the present invention.

Generally speaking, they may be prepared according to methods well known in this art.

Antibodies generated against the polypeptides or polynucleotides of the invention can be obtained by administering the polypeptides or polynucleotides of the invention, or epitope-bearing fragments of either or both, analogues of either or both, or cells expressing either or both, to a human or animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495-497 (1975); Kozbor et al., *Immunology Today* 4: 72 (1983); Cole et al., pg. 77-96 in MONOCOLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms such as other mammals, can be used to express humanized antibodies immunospecific to the polypeptides or polynucleotides of the invention.

An anti-idiotypic antibody can furthermore be raised against an antibody or other specific binding partner according to the present invention, and such an antibody can then serve as a substitute for the original antigen in the uses according to the present invention.

Uses of the Materials of the Invention

The measurement of serum LH or hCG is an integral part of diagnostic tests in human infertility, reproductive failure and pregnancy disorders. Our findings provide a novel, measurable diagnostic marker for human infertility, pregnancy disorders, ovarian, testicular cancer and Alzheimer's disease. In addition, circulating sLHCGR will allow the simultaneous measurement of both free hormone (LH and hCG) and sLHCGR-bound hormone, thus facilitating measurement of active hormone levels in specific clinical conditions.

Generally speaking, therefore, the materials of the present invention, including complexes of the LHCGR polypeptide with reproductive hormones, can be used in the treatment and diagnosis of conditions associated with over- and under-production of the said receptor, with over- and under-production of luteinising hormone, with over- and under-production of chorionic gonadotropin, with reproductive failure, with gonadal cancer and metastases, and with Alzheimer's disease.

The levels of LH and hCG are currently used as markers to detect various clinical conditions. Target tissues for LH/hCG and clinical conditions where free serum or urine LH/hCG concentrations are measured are described below: LH target tissues—ovary; testis; uterine endometrium hCG target tissues—corpus luteum (pregnant women); foetal tissue; ovary; testis; placenta; uterine blood vessels; foetal blood vessels and brain; uterine muscles.

Low serum LH may generally be associated with infertility and sterility.

High serum LH may generally be associated with polysystic ovarian syndrome, ovarian cancer and testicular cancer.

High serum hCG may generally be associated with molar pregnancy, Down's syndrome, intra-uterine growth restriction and pre-eclampsia.

Human LH and hCG concentrations in body fluids (primarily serum and urine) are measured in a variety of clinical conditions described below. This invention will be significant wherever these two hormones are used as diagnostic biomarkers. This is because both hormones can bind the same soluble receptor in the body fluids. Therefore, the measurement of hCG and its soluble receptor (sLHCGR) in the same sample will allow the determination of functionally active circulating LH/hCG in a given clinical condition.

The present invention therefore has diagnostic applications in the following areas of human reproductive medicine:

A. Assisted Reproductive Technology

1. Human Infertility

The sLHCGR is a normal component of LH/hCG receptor systems. However, the amount of sLHCGR in individuals could be variable in both sexes. It is expected that when blood levels of sLHCGR are high, LH and hCG will be less functionally available and that fertility levels in both sexes could be linked to blood sLHCGR concentrations.

One of the causes of human infertility is the antibody in seminal plasma or autoantibody against ovarian antigen.[9] Human sperm and seminal vesicles produce large quantities of LHCGR.[12,20] Therefore, it is expected that sLHCGR might be detected in human semen, and possible that women might raise is antibodies to epitopes of their partner's LHCGR. Therefore, assays could be developed to detect both sLHCGR concentrations in men's semen and antibody in women's blood as a diagnostic test for infertility.

Therefore, in a further aspect, the present invention provides a method of diagnosing a risk of male or female infertility or difficulty to conceive in a human or non-human animal patient, which comprises assaying a sample of body fluid (e.g. serum (blood), urine or semen) removed from the patient to determine the presence of a soluble LHCGR polypeptide according to the present invention or an antibody thereto. The presence of high concentrations of soluble LHCGR polypeptide in the male body fluid or high concentrations of antibodies thereto in the female body fluid may suggest or be diagnostic of a risk of male or female infertility or difficulty to conceive.

In a further aspect of the present invention, there is provided the use of an antibody or other specific binding partner to the soluble LHCGR polypeptide according to the present invention, or the use of an anti-idiotypic antibody or other specific binding partner to a naturally occurring antibody to the soluble LHCGR polypeptide according to the present invention, in the preparation of a composition for use in an assay for diagnosing a risk of male or female infertility or difficulty to conceive in a human or animal patient by the above method.

2. Ovarian Hyperstimulation

This treatment has two components: a) Blocking physiological ovarian functions by GnRH agonists (buserelin/nafarelin) or antagonists (cetrorelix) at the outset and b) subsequent stimulation of the ovary by FSH, LH and hCG (FIG. 1). The function of LH/hCG would however depend upon the relative concentrations of sLHCGR in the blood and mLHCGR on the ovarian cell surface. The response, dose and the frequency of administration of these hormones could be determined by the concentration of sLHCGR in the circulation. Therefore, analysis of the serum concentration of sLHCGR before and during ovarian hyperstimulation could act as a marker for the efficiency of hormone treatment.

Therefore, in a further aspect, the present invention provides a method of diagnosing impaired ovarian hyperstimulation in assisted reproduction methods in a female human or non-human animal patient, which comprises assaying a sample of body fluid (e.g. serum (blood) or urine) removed from the patient to determine the presence of a soluble LHCGR polypeptide according to the present invention. The presence of certain proportions of the soluble LHCGR polypeptide in the body fluid relative to cell-bound LHCGR receptor may suggest or be diagnostic of impaired ovarian hyperstimulation in an assisted reproduction method.

In a further aspect of the present invention, there is provided the use of an antibody or other specific binding partner to the soluble LHCGR polypeptide according to the present invention in the preparation of a composition for use in an assay for diagnosing impaired ovarian hyperstimulation in an assisted reproduction method in a female human or non-human animal patient by the above method.

3. Egg Maturation and sLHCGR in Follicular Fluid

The maturation of the egg, ovulation as well as luteinisation of the ovarian cells are determined by the degree of interaction between LH and mLHCGR expressed in the ovary. We have demonstrated that the follicular fluid in the hyperstimulated ovaries contain sLHCGR. It is expected that high levels of sLHCGR in the follicular fluid might result in a lower LH interaction with mLHCGR and incomplete maturation of eggs. Therefore, measurement of the free sLHCGR in follicular fluid could provide a diagnostic marker for egg maturation.

Therefore, in a further aspect, the present invention provides a method of diagnosing impaired egg maturation or a susceptibility thereto in a female human or non-human animal patient, which comprises assaying a sample of body fluid (e.g. follicular fluid) removed from the patient to determine the presence of a soluble LHCGR polypeptide according to the present invention. The presence of high level of the soluble LHCGR polypeptide in the body fluid may suggest or be diagnostic of impaired egg maturation or a susceptibility thereto.

In a further aspect of the present invention, there is provided the use of an antibody or other specific binding partner to the soluble LHCGR polypeptide according to the present invention in the preparation of a composition for use in an assay for diagnosing impaired egg maturation or a susceptibility thereto in a female human or non-human animal patient by the above method.

4. Polycystic Ovarian Syndrome (PCOS)

About 5-10% women of childbearing age have PCOS characterised by anovulation, amenorrhea, varying degrees of insulin resistance, and high serum testosterone and LH. There is no specific diagnostic test for PCOS. However a combination of biochemical tests including measurements of serum LH are routinely carried out. An estimation of free and bound LH could have additional diagnostic implications.

Therefore, in a further aspect, the present invention provides a method of diagnosing PCOS or a susceptibility thereto in a female human or non-human animal patient, which comprises assaying a sample of body fluid (e.g. serum (blood) or urine) removed from the patient to determine the presence of a soluble LHCGR polypeptide according to the present invention. The presence of low levels of the soluble LHCGR polypeptide in the body fluid may suggest or be diagnostic of PCOS or a susceptibility thereto.

In a further aspect of the present invention, there is provided the use of an antibody or other specific binding partner to the soluble LHCGR polypeptide according to the present invention in the preparation of a composition for use in an assay for diagnosing PCOS or a susceptibility thereto in a female human or animal patient by the above method.

B. Pregnancy Failure and Pregnancy Disorders

1. Miscarriage

Low serum concentrations of hCG at very early pregnancy (6-8 wks) is used as a diagnostic marker for high risk pregnancies. The assay for receptor-bound hCG could have additional diagnostic significance.

Therefore, in a further aspect, the present invention provides a method of diagnosing a risk of miscarriage in a female human or non-human animal patient, which comprises assaying a sample of body fluid (e.g. serum (blood) or urine) removed from the patient to determine the presence of a soluble LHCGR polypeptide according to the present invention. The assay may be particularly useful within the first 8 weeks of pregnancy. The presence of high levels of the soluble LHCGR polypeptide in the body fluid may suggest or be diagnostic of a risk of miscarriage.

In a further aspect of the present invention, there is provided the use of an antibody or other specific binding partner to the soluble LHCGR polypeptide according to the present invention in the preparation of a composition for use in an assay for diagnosing a risk of miscarriage in a human or animal patient by the above method.

2. Down's Syndrome and Other Trisomic Pregnancies

A large number of serum and urine biochemical markers (alpha fetoprotein, unconjugated estriol, pregnancy associated plasma protein A and activin) are used in various combination for the diagnosis of the genetically compromised pregnancies. However, measurement of total and free hCG$\beta$ at the first and second trimester is the most common parameter in all the diagnostic tests.

Therefore, in a further aspect, the present invention provides a method of diagnosing Down's syndrome and other trisomic pregnancy conditions or a susceptibility thereto in a female human or non-human animal patient, which comprises assaying a sample of body fluid (e.g. serum (blood) or urine) removed from the patient to determine the presence of a soluble LHCGR polypeptide according to the present invention. The presence of high levels of the soluble LHCGR polypeptide in the body fluid may suggest or be diagnostic of Down's syndrome and other trisomic pregnancy conditions or a susceptibility thereto.

In a further aspect of the present invention, there is provided the use of an antibody or other specific binding partner to the soluble LHCGR polypeptide according to the present invention in the preparation of a composition for use in an assay for diagnosing Down's syndrome and other trisomic pregnancy conditions or a susceptibility thereto in a human or animal patient by the above method.

3. Molar Pregnancies

Serum hCG is high in these pregnancies. This indicates that levels of soluble LHCGR polypeptide in the serum may be too low to complex with free serum hCG.

Therefore, in a further aspect, the present invention provides a method of diagnosing molar pregnancy or a susceptibility thereto in a human or non-human animal patient, which comprises assaying a sample of body fluid (e.g. serum (blood) or urine) removed from the patient to determine the presence of a soluble LHCGR polypeptide according to the present invention. The presence of low levels of the soluble LHCGR polypeptide in the body fluid may suggest or be diagnostic of molar pregnancy or a susceptibility thereto.

In a further aspect of the present invention, there is provided the use of an antibody or other specific binding partner to the soluble LHCGR polypeptide according to the present invention in the preparation of a composition for use in an assay for diagnosing molar pregnancy or a susceptibility thereto in a human or animal patient by the above method.

4. Pre-Eclampsia and Intra-Uterine Growth Restriction (IUGR)

Currently, pre-eclampsia and IUGR are diagnosed by ultrasound at late pregnancy (22-30 wks). Recently, soluble Flt-1 receptor for vascular endothelial growth factor has been shown to increase in serum at late pregnancy (20-30 wks of gestation). While soluble Flt-1 in combination with placental growth factor (PIGF) could be diagnostic markers for pre-eclampsia at late pregnancy,[37, 38] there is no specific serum marker to detect the onset of these diseases in early pregnancy. We have established that the serum concentration of sLHCGR could be measured as early as 8-10 wks of pregnancy and therefore could be a superior prognostic marker for pre-eclampsia and IUGR at early pregnancy. Early prognosis or diagnosis of pre-eclampsia and IUGR will markedly improve the survival rate for mothers and babies.

Therefore, in a further aspect, the present invention provides a method of diagnosing pre-eclampsia or IUGR or a susceptibility thereto in a female human or non-human animal patient, which comprises assaying a sample of body fluid (e.g. serum (blood) or urine) removed from the patient to determine the presence of a soluble LHCGR polypeptide according to the present invention. The assay may be particularly useful as a prognostic tool within the first 20 weeks of pregnancy, for example between about 8 and about 20 weeks of pregnancy. The presence of high levels of the soluble LHCGR polypeptide in the body fluid may suggest or be diagnostic of pre-eclampsia or IUGR or a susceptibility thereto.

In a further aspect of the present invention, there is provided the use of an antibody or other specific binding partner to the soluble LHCGR polypeptide according to the present invention in the preparation of a composition for use in an assay for diagnosing pre-eclampsia or IUGR or a susceptibility thereto in a female human or animal patient by the above method.

C. Testicular and Ovarian Cancers

In addition to physical examination, the laboratory tests for testicular cancer include serum alpha-fetoprotein and hCG. In some forms of ovarian cancer (germ cells), the levels of serum alpha-fetoprotein and hCG are elevated.

Therefore, in a further aspect, the present invention provides a method of diagnosing testicular or ovarian cancer or a susceptibility thereto in a human or non-human animal patient, which comprises assaying a sample of body fluid (e.g. serum (blood), urine or semen) removed from the patient to determine the presence of a soluble LHCGR polypeptide according to the present invention. The presence of high levels of the soluble LHCGR polypeptide in the body fluid may suggest or be diagnostic of testicular or ovarian cancer or a susceptibility thereto.

In a further aspect of the present invention, there is provided the use of an antibody or other specific binding partner to the soluble LHCGR polypeptide according to the present invention in the preparation of a composition for use in an assay for diagnosing testicular or ovarian cancer or a susceptibility thereto in a human or animal patient by the above method.

D. Alzheimer's Disease

Alzheimer's disease (AD) is a neuro-degenerative disorder which often affects more women than men. Until recently, it was thought to be due to the lack of estrogen. As a result, hormone replacement (HRT) therapy was developed in part to reduce the susceptibility of women to Alzheimer's disease. However, recent studies demonstrate that LH is a major factor in AD pathogenesis. The patients with AD have elevated levels of LH when compared with controls, and both LH and its receptor are present in increased quantities in brain hippocampus, pyramidal neurons and neurofibrillary tangles susceptible to degeneration (Casadesus G, Atwood C S, Zhu X, Hartzler A W, Webber K M, Perry G, Bowen R L, Smith M A. Evidence for the role of gonadotropin hormones in the development of Alzheimer disease. Cell Mol Life Sci. 62:293-298, 2005).

This suggests that the level of serum soluble LHCGR may be indicative of a susceptibility to Alzhemier's disease.

Therefore, in a further aspect, the present invention provides a method of diagnosing Alzheimer's disease or a susceptibility thereto in a human or non-human animal patient, which comprises assaying a sample of body fluid (e.g. serum (blood), urine or semen) removed from the patient to determine the presence of a soluble LHCGR polypeptide according to the present invention. The assay may be particularly useful in elderly persons or those who are otherwise at a higher than normal risk of the disease. The presence of particular levels of the soluble LHCGR polypeptide in the body fluid may suggest or be diagnostic of Alzheimer's disease or a susceptibility thereto.

In a further aspect of the present invention, there is provided the use of an antibody or other specific binding partner to the soluble LHCGR polypeptide according to the present invention in the preparation of a composition for use in an assay for diagnosing Alzheimer's disease or a susceptibility thereto in a human or animal patient by the above method.

The assay methods mentioned above are suitably selected from known specific protein assays, and may be qualitative or quantitative or semi-quantitative. Quantitative specific protein binding assays are preferred. A variety of such assays are commercially available, as will be well known to those skilled in this art. These assays may, for example, be direct binding immunoassays or solid-phase immunoassays. Solid-phase immunoassays are preferred in the present invention. Such assays may, with simple modifications according to the different species to be assayed, be used to measure free soluble LHCGR polypeptide, free complexes of soluble LHCGR polypeptide and hormone, and free uncomplexed hormone, amongst others. Particularly preferred are specific immunoassays such as enzyme-linked immunosorbent assays (ELISA) and radio-immunometric assays (RIMA).

It is preferred that the sample of body fluid obtained from the patient is pre-treated to assist the subsequent assay procedure. For example, tissue components such as cells or spermatozoa may be removed, e.g. by centrifugation, and other protein components such as albumin and globulin may be removed by standard methods to prevent possible interference or masking of the assay results.

The present invention also has therapeutic and/or prophylactic applications, particularly in the following areas of human reproductive and other medicine:

A. Down's Syndrome, Polycystic Ovarian Syndrome and Other Pregnancy Disorders

As described above, one of the important aspects of this invention is that sLHCGR detected in serum and follicular fluid is capable of binding the hormones LH and hCG. This aspect of the observation has therapeutic significance on the basis that the functionally active free hormone concentration in blood could be inversely related to the sLHCGR concentration. Therefore, high serum sLHCGR could have a pathological effect in various clinical conditions. For example, in Down's syndrome (DS) and in other pregnancy disorders, total serum hCG concentrations are high. However, as described below (FIG. 5), the sLHCGR concentrations in DS pregnancies are also significantly higher compared to those of normal pregnancies. This suggests that active free hCG available for physiological maintenance of pregnancy could be significantly lower than that of normal pregnancy. A parallel situation exists in women with PCOS where serum LH concentrations are usually high.

The goal of the therapeutic application would be to achieve physiological concentrations of hormones by employing antagonists (specific binding partners) that prevent sLHCGR from binding to LH or hCG hormones in the blood. The antagonists could be of at least two different forms: humanized monoclonal antibodies against sLHCGR which can neutralize its hormone binding activity, or in vitro designed compounds which could specifically target and block the hormone binding sites of sLHCGR. Antibodies (also called immunoglobulins) are proteins which are produced and secreted by a special type of blood cells (B lymphocytes) in response to foreign substances (antigen). Monoclonal antibodies are a homogeneous population of proteins produced against a specific region of the protein (epitope) and are secreted by a single clone.

Therefore, in a further aspect, the present invention provides a method of treating or preventing a disease or condition selected from Down's syndrome, polycystic ovarian syndrome and other pregnancy disorders in a female human or non-human animal patient suffering therefrom or susceptible thereto, which comprises administering to the patient an effective amount of one or more agent selected from the soluble LHCGR polypeptide according to the present invention, an antibody or other specific binding partner thereto and an anti-idiotypic antibody to such an antibody or specific binding partner.

In a further aspect of the present invention, there is provided the use of one or more agent selected from the soluble LHCGR polypeptide according to the present invention, an antibody or other specific binding partner thereto, and an anti-idiotypic antibody to such an antibody or specific binding partner, in the preparation of a composition or compositions for treating or preventing a disease or condition selected from Down's syndrome, polycystic ovarian syndrome and other pregnancy disorders in a female human or non-human animal patient suffering therefrom or susceptible thereto by the above method.

The treatment and composition(s) may if desired further comprise one or more further active and/or inactive agents, as will be well within the normal knowledge of those skilled in this art. For example, effective amounts of one or more reproductive hormone such as hCG or LH may be co-administered in the treatment. The use of appropriate carriers and other inactive materials in the compositions is discussed further below.

B. Alzheimer's Disease

Similarly, the present invention further provides a method of treating or preventing Alzheimer's disease in a human or non-human animal patient suffering therefrom or susceptible thereto, which comprises administering to the patient an effective amount of one or more agent selected from the soluble LHCGR polypeptide according to the present invention and an antibody or other specific binding partner thereto.

The invention further provides the use of one or more agent selected from the soluble LHCGR polypeptide according to the present invention and an antibody or other specific binding partner thereto in the preparation of a composition or compositions for treating or preventing Alzheimer's disease in a human or non-human animal patient suffering therefrom or susceptible thereto by the above method.

As in the case of the treatment of pregnancy disorders discussed above, the treatment and composition(s) for Alzheimer's disease may if desired further comprise one or more further active and/or inactive agents, such as one or more reproductive hormones such as hCG or LH.

Other related uses of the materials according to the present invention can also be identified.

Thus, for example, a nucleotide sequence according to the invention may be used as a hybridisation probe for RNA, cDNA and genomic DNA to isolate full-length cDNAs and genomic clones encoding soluble polypeptide according to the invention and to isolate cDNA and genomic clones of other genes that have a high identity, particularly high sequence identity, to the LHCGR gene.

The nucleotide sequence may include, for example, unprocessed RNAs, ribozyme RNAs, hair-pin RNAs for use as interference RNAs, small interfering RNAs (siRNAs), mRNAs, cDNAs, genomic DNAs, B-DNAs, E-DNAs and Z-DNAs.

The antibodies can be employed to isolate or to identify clones expressing the polypeptides or polynucleotides of the invention or to purify the polypeptides or polynucleotides by, for example, affinity chromatography.

The polynucleotides, polypeptides and antibodies that bind to or interact with a polypeptide of the present invention can also be used to configure screening methods for detecting the effect of added compounds on the production of mRNA or polypeptide in cells. For example, an ELISA assay can be constructed for measuring secreted or cell associated levels of polypeptide using monoclonal and polyclonal antibodies by standard methods known in the art. This can be used to discover agents which can inhibit or enhance the production of polypeptide (also called antagonist or agonist, respectively) from suitably manipulated cells or tissues.

The materials of the present invention can also be used to screen for compounds which agonise or antagonise the cell-bound (mature) LHCG receptor in vivo. The method of screening can involve high-throughput techniques. For example, to screen for agonists or antagonists, a synthetic reaction mix, a cellular compartment, such as a membrane, cell envelope or cell wall, or a preparation of any thereof, comprising soluble LHCGR polypeptide and a labelled substrate or ligand of such polypeptide is incubated in the absence or the presence of a candidate molecule that may be a soluble LHCGR agonist or antagonist. The ability of the candidate molecule to agonize or antagonize the LHCGR polypeptide is reflected in decreased binding of the labelled ligand or decreased production of product from such substrate. Detection of the binding interaction can be enhanced using a reporter system, as is known in this art. Reporter systems that can be useful in this regard include but are not limited to colorimetric, labelled substrate converted into product, a reporter gene that is responsive to changes in LHCGR polynucleotide or polypeptide activity, and binding assays known in the art.

Inhibitors of the soluble LHCGR in vivo may be identified, in a generally similar manner, in suitable screens in which a candidate compound is screened for its ability to bind to soluble LHCGR polypeptides according to the present invention. Such screens may be carried out in respect of a plurality of compounds, for example, from a compound library.

An agonist or antagonist of the cell-bound receptor, or an inhibitor of the soluble receptor, identified using such a screen may be synthesised and formulated into a pharmaceutical composition for use.

Compositions and Delivery Routes

For the in vitro aspects of the present invention—e.g. the preparation and handling of materials or the performance of assays—the polypeptide, polynucleotide, antibody or other specific binding partner, or other active agent(s), are typically carried and used in conventional carrier systems and compositions, for example aqueous media, preferably adapted for the particular purpose, in ways which will be well known to those skilled in this art.

For the in vivo—e.g. the therapeutic—aspects of the present invention, the polypeptide or an antibody or other specific binding partner thereto, or other active agent(s), is/are preferably supplied to a patient by injection. Alternatively, the polypeptide or its specific binding partner may be supplied orally or topically. Any composition form which is suitable for the desired administration route may be used to deliver the material(s) to the desired location within the patient, as will be well known to those of ordinary skill in this art.

Preferably, the active agent(s) is/are supplied to a patient by intra-arterial, intravenous, intramuscular, intra-peritoneal or subcutaneous injection.

Where more than one active agent is to be delivered to the patient, the different agents may be administered simultaneously or sequentially.

BRIEF DESCRIPTION OF THE DRAWINGS

Embodiments of the present invention will now be described, by way of example only, and with reference to the accompanying drawings, in which.

DETAILED DESCRIPTION OF THE DRAWINGS

Figure 1:
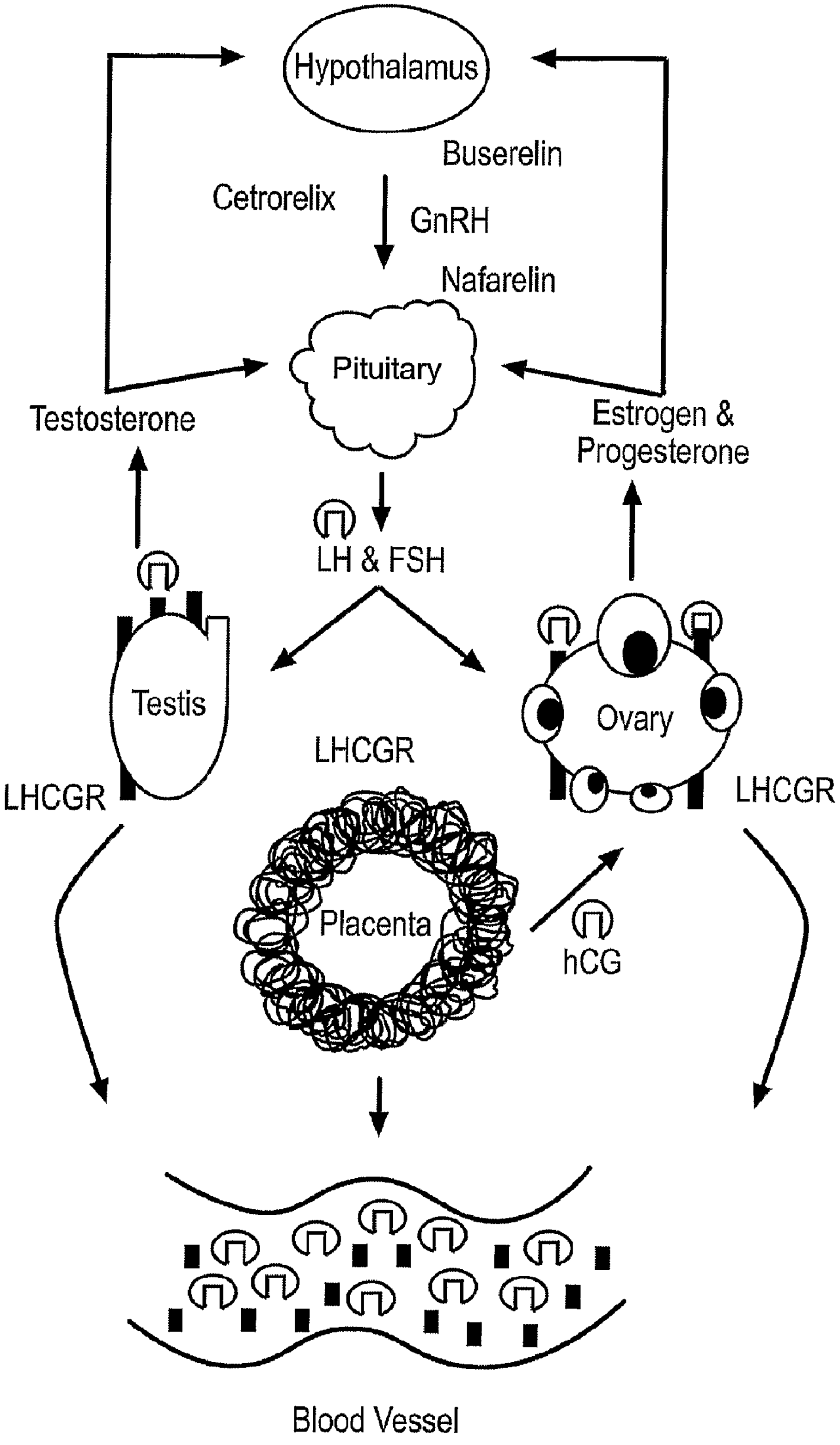
FIG. 1 shows a schematic representation of the functions of the reproductive hormones FSH, LH and hCG in spermatogenesis, egg maturation, ovulation and ovarian hyperstimulation.

Referring firstly to FIG. 1, this shows schematically the functions of the reproductive hormones FSH, LH and hCG in spermatogenesis, egg maturation, ovulation and ovarian hyperstimulation.

The hypothalamus releases GnRH which stimulates FSH and LH secretion from the pituitary. FSH stimulates sperm production and maturation of the ovarian follicles. LH induces the production and secretion of sex steroids from gonads i.e., testosterone and oestrogen. In males, LH binds to its receptor on Leydig cells and facilitates the production and secretion of testosterone. In the ovary, LH binds to thecal cells and stimulates the production of testosterone which is converted to oestrogen by neighbouring granulosa cells. Additionally, in females, an LH surge facilitates the ovulation and luteinisation of the ovary (corpus leuteum) following release of the egg. The hCG produced by the placenta sustains the corpus leuteum which secretes progesterone and oestradiol that are vital for implantation of the embryo. Oestrogen and testosterone negatively regulate GnRH, LH and FSH production. In ovarian hyperstimulation treatment, the production of natural FSH and LH is blocked by GnRH agonists (Buserelin, Nafarelin) or antagonists (Cetrorelix) and maturation of eggs is induced by exogenously injected FSH, LH and hCG. The LH and hCG have the same receptor, LHCGR. This receptor has at least two forms, including the membrane bound mature (mLHCGR) form as known in the prior art and the free soluble (sLHCGR) form the subject of the present invention. The sLHCGR released into the circulation can bind LH/hCG and can interfere with their functions. The data reported below show that sLHCGR is released into the circulation and binds LH and hCG hormones.

Figure 2:
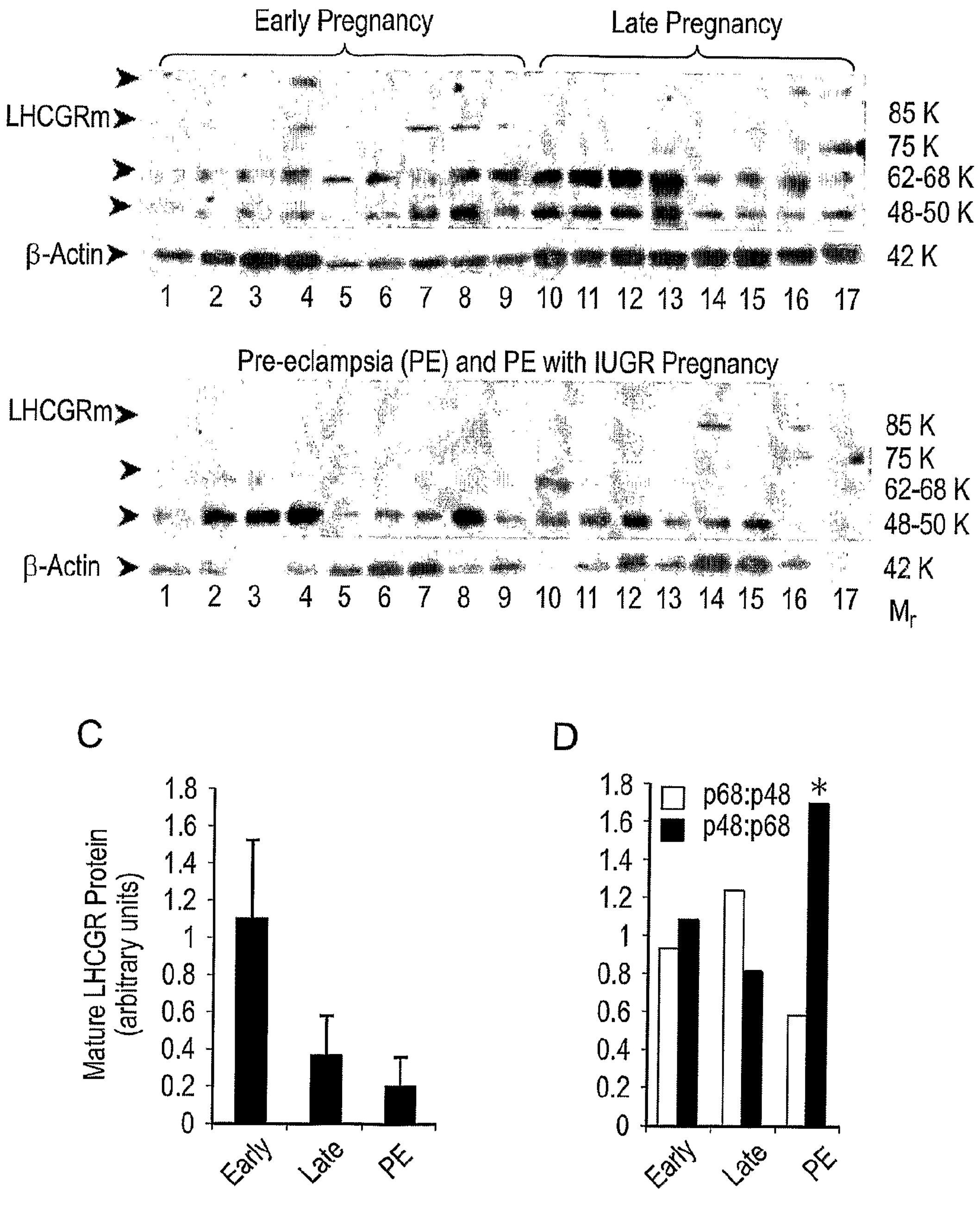
FIG. 2 shows (top blot and lower blot) Western blots of LHCGR protein isoforms in (top blot) normal human placenta and (lower blot) human placenta in pre-eclampsia (PE) patients and in PE patients with intra-uterine growth restriction (IUGR); (C) quantitative expression of mature LHCGR protein in early pregnancies, late pregnancies and in PE pregnancies; and (D) quantitative ratios of p68:p48 (white bars) and p48:p68 (black bars) LHCGR isoforms (p68=MW c. 68; p48=MW c. 48) in early pregnancies, late pregnancies and in PE pregnancies.

FIG. 2 shows the occurrence of various LHCGR protein isoforms expressed in normal placenta and in placenta from patients with pre-eclampsia (PE) and PE with intra-uterine growth restriction (IUGR). PE was defined as gestational hypertension with proteinurea which developed for the first time in labour or in puerperium. Gestational hypertension was defined as systolic blood pressure ≧140 mm Hg and diastolic blood pressure ≧90 mmHg. Proteinurea was defined as ≧300 mg total protein in 24 h collection or 2-3+ by dipsick on two consecutive measurements separated by 4-5 h. IUGR was defined as a birth weight below the $5^{th}$ percentile of the reference group.

$LHCGR_m$=mature functional LHCGR; $M_r$, relative molecular mass of the proteins. *, $P<0.05$.

In this test, the concentrations of LHCGR are measured relative to β-Actin, an unchanging internal control.

The placental tissue extract containing 15-20 μg of total protein was loaded on each lane and was separated in 9% polyacrylamide-sodium dodecyl sulphate (SDS) gels under reducing conditions. The proteins were transferred to PVDF membrane (Immobilon P, Millipore, Watford, UK), and immunoreacted with a mouse monoclonal antibody against human LHCGR (LHR-29). Immuno-stained Western blots were developed using enhanced chemi-luminescence (ECL) reagent (Amersham Biosciences, Buckinghamshire, UK) as decscribed in Banerjee et al., Quantitative recovery of immunoreactive proteins from clinical samples following isolation of RNA and DNA, BioTechniques 35: 450-456, 2003.

In order to quantify the LHCGR isoforms, the blots were stripped and re-probed with anti-human mouse β-Actin monoclonal antibody, clone 15 (Sigma, UK). The intensity of the bands was measured by densitometric scanning (Alpha-Imager) the bands of the experimental samples and the values were normalized to that of β-Actin.

The top blot in FIG. 2 shows Western blots of proteins from samples of normal early (8-12 weeks (wks)) (lanes 1 to 9) and late (36-39 wks) (lanes 10 to 17) human placenta. At least 5-6 isoforms of LHCGR including the membrane-bound functional $LHCGR_m$ (85 kD) and soluble sLHCGR (MW 45-48 k) proteins are visible.

The lower blot in FIG. 2 shows Western blots of proteins from samples obtained from patients with PE (lanes 1 to 12, 15 and 17) or PE with IUGR (lanes 13, 14 and 16).

FIG. 2C shows quantitatively the expression of the mature $LHCGR_m$ in early, late pregnancies and in PE pregnancies.

FIG. 2D shows quantitatively the relative expression of LHCGR isoforms p48 and p68, presented as p68:p48 or p48:p68.

This test shows that the expression of sLHCGR (p48) is significantly higher in PE than in control (normal) pregnancies.

Figure 3:
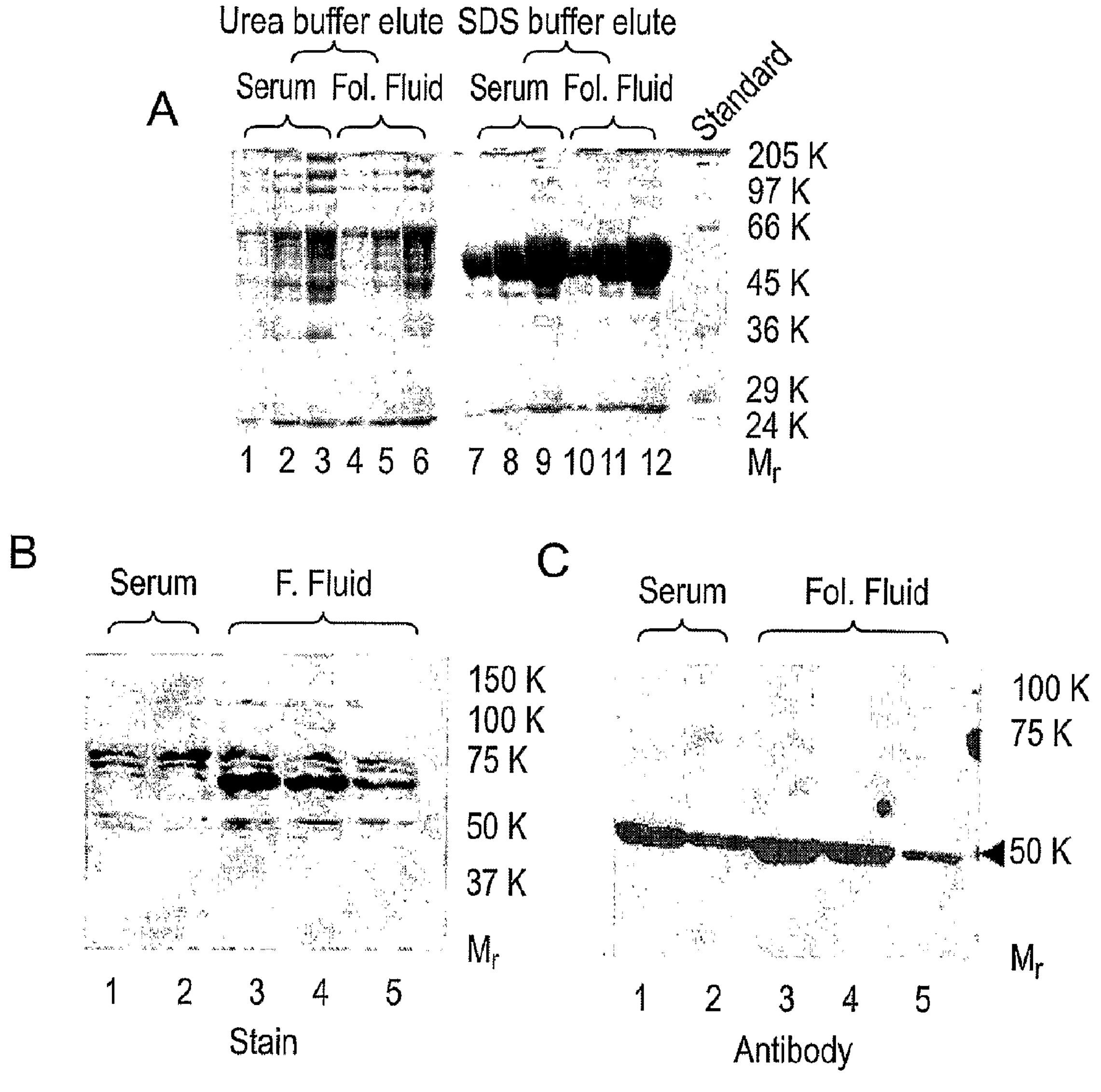
FIG. 3 shows (A) Western blots of serum from a 12-week pregnant woman and follicular fluid from a woman undergoing ovarian hyperstimulation, at three concentrations each and using two elution buffers, as described; (B) Western blots of sera from two 12-week pregnant women and follicular fluid from three women undergoing ovarian hyperstimulation, as described; and (C) Western blots of samples corresponding to the samples in B after exposure to anti-human LHCGR antibody, as described.

FIG. 3 shows the results of tests to show that the soluble LHCGR of the present invention is detectable in the human serum and follicular fluid.

In the tests the results of which are shown in FIG. 3A, the human serum from a woman of 12 wks pregnancy and follicular fluid from a woman undergoing ovarian hyperstimulation (as is done in in vitro fertilisation (IVF) procedures) were absorbed to Proteoprep Blue resin (Proteoprep Kit, Sigma). The albumin and globulin depleted proteins were eluted by an urea-based equilibration buffer and three concentrations for each sample (lanes 1-6; 5, 10 and 20 μg) and the corresponding bound proteins released by SDS-buffer (lanes 7-12) were loaded on an 8% polyacrylamide SDS gel and stained with 0.25% Coomassie Brilliant blue R (Sigma) in methanol (40%)-acetic acid (10%).

In the tests the results of which are shown in FIGS. 3B and 3C, albumin and globulin depleted sera from two 12 wk pregnant women (lanes 1 and 2) and follicular fluid from three women undergoing ovarian hyperstimulation (lanes 3 to 5) were separated in a 9% polyacrylamide-SDS gel, blotted (B) and immunoreacted (C) with anti-human LHCGR (LHR 29) antibody. The arrow (C, lanes 1-5) indicates the ~48-50 kD (~48-50 k) band in serum and follicular fluid that reacted with the antibody.

The tests reported in FIG. 3 show that the soluble LHCGR is present in serum and follicular fluid and is detectable by standard techniques.

Figure 4:
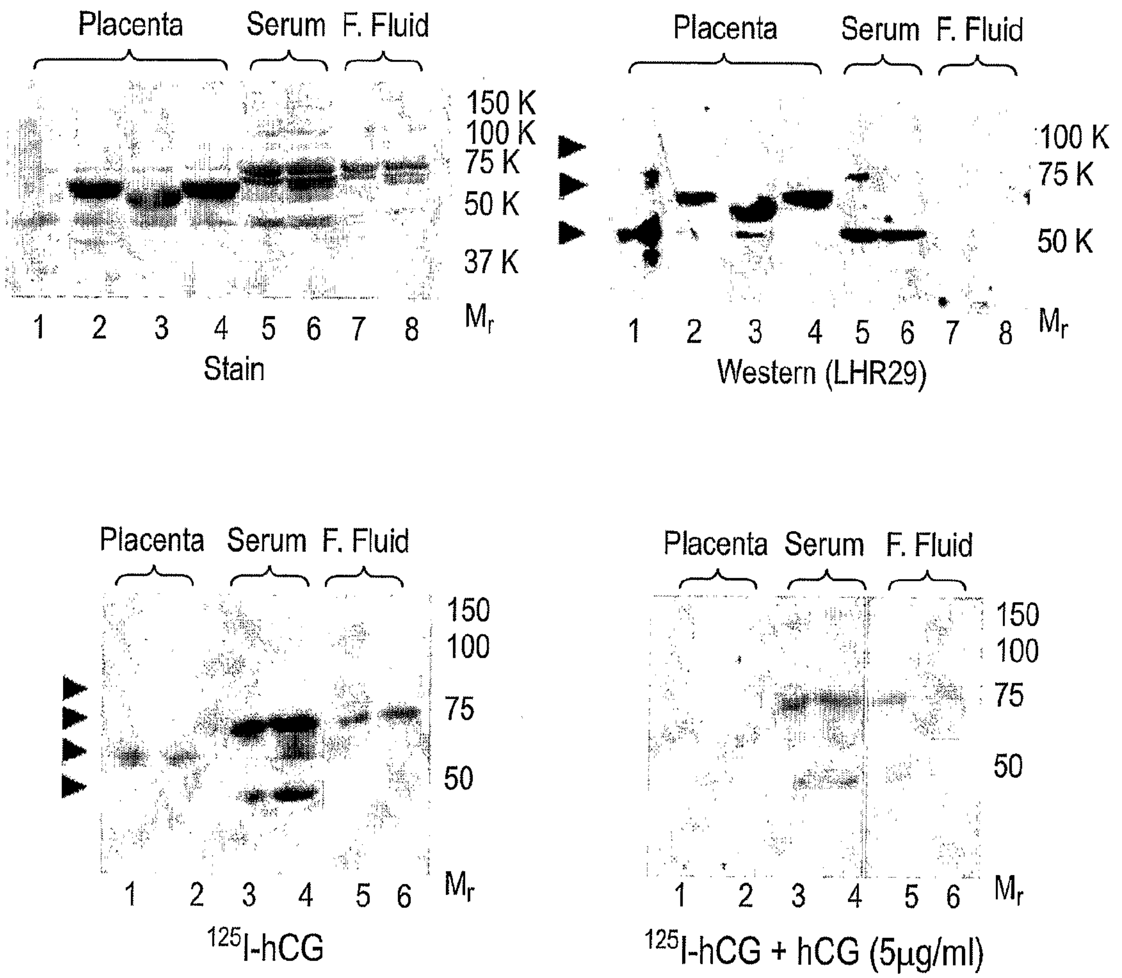
FIG. 4 shows (top left blot) Western blots of LHCGR protein isoforms in late placental tissue, serum and follicular fluid, as described; (top right blot) Western blots of samples corresponding to the samples in the top left blot after exposure to anti-human LHCGR antibody, as described; (lower left blot) Western blots of LHCGR protein isoforms in late placental tissue, serum and follicular fluid after exposure to radiolabelled hCG hormone, as described; and (lower right blot) Western blots of samples corresponding to the samples in the lower left blot after exposure to radiolabelled hCG hormone and unlabelled recombinant hCG hormone, as described.

FIG. 4 shows the results of tests to show that the serum and follicular fluid sLHCGR are similar to that observed in late placental tissues in Western blot.

The extracts from term placenta (lanes 1-4) and albumin-globulin depleted serum (lanes 5-6) and follicular fluid (lanes 7-8) were heat-denatured under non-reducing (lanes 1, 3, 5 and 7) or reducing conditions (lanes 2, 4, 6 and 8), FIG. 4A, Coomassie brilliant blue stain; FIG. 4B, chemi-luminescence following antibody reaction. FIGS. 4C and 4D, ligand blots of placenta, serum and follicular fluid proteins with $^{125}$I-hCG. The albumin-globulin depletion from serum (lanes 3-5) and follicular fluid (lanes 6-8) was carried out exactly as described in FIG. 3 except that a salt-based (25 mM Tris-Cl, pH 7.5 and 150 mM NaCl) instead of urea-based equilibration buffer was used and eluted proteins were heat denatured (lanes 3 and 5), denatured under reducing (lanes 1, 2, 4 and 6) conditions. The blots were blocked for 1 h at 25° C. in the presence of 1% casein followed by incubation in the presence (C) of 0.1 μCi/ml of $^{125}$I-hCG (PerkinElmer, USA) or (D) $^{125}$I-hCG plus 5 μg/ml of unlabelled recombinant hCG (Sigma, UK). Notably, in addition to 50 kD sLHCGR, a 75 kD LHCGR isoform is strongly binding to $^{125}$I-hCG in serum and follicular fluid samples (indicated by arrows).

Figure 5:
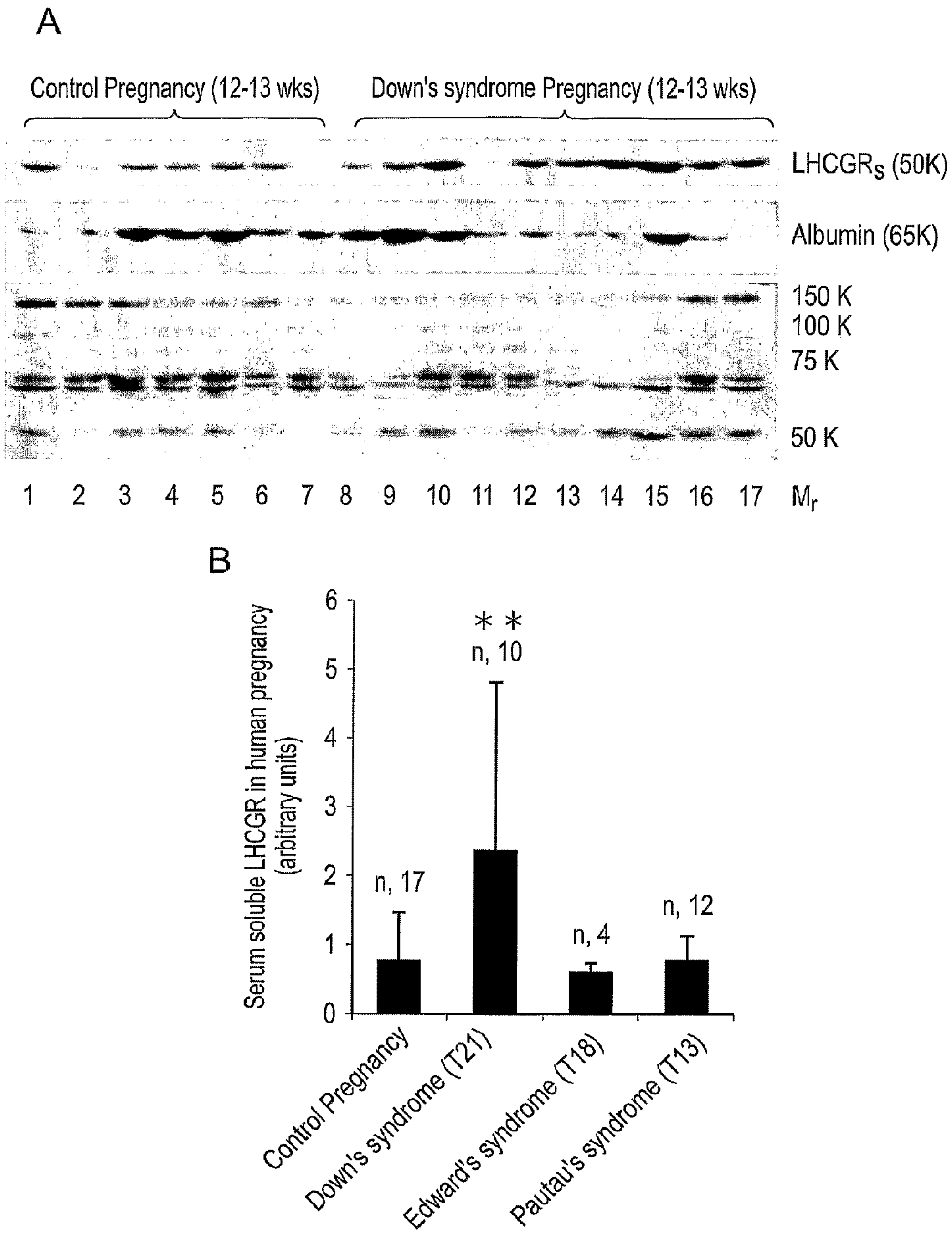
FIG. 5 shows (A) Western blots of LHCGR isoforms in serum from women with normal (control) and Down's syndrome pregnancies, as described (A, top panel: after immunostaining with mouse monoclonal anti-LHCGR antibody; A, middle panel: after further exposure to mouse monoclonal anti-human serum albumin; A, lower panel: after staining with Coomassie blue); and (B) quantitative expression of serum soluble LHCGR (sLHCGR) in various pregnancy conditions as stated.

FIG. 5 shows the results of tests to show that the serum concentrations of soluble LHCGR of the present invention in early Down's syndrome pregnancies (11 to 13 wks) are significantly higher compared with those of age-matched control (normal) pregnancies.

The albumin-globulin depleted serum proteins (see the discussion of FIG. 4 above) from early human pregnancy were resolved in 9% polyacrylamide-SDS PAGE, electro-transferred to membrane (Immobilon P, Millipore, UK) and was first immunostained with mouse monoclonal anti-LHCGR antibody (LHR 29) (FIG. 5A, top panel) and subsequently to the mouse monoclonal anti-human serum albumin (Clone ab10242, abcam, Cambridge, UK) which recognizes 65 kD band (FIG. 5A, middle panel). The same blot was stained with Coomassie blue (FIG. 5A, bottom panel). B, quantitative estimation of the serum $LHCGR_s$ concentrations in Down's syndrome and other trisomics pregnancies; The intensity of soluble LHCGR ($LHCGR_s$) bands in the experiments shown in FIG. 5A and others were normalised with albumin band as internal controls.

The results demonstrate that $LHCGR_s$ concentration in Down's syndrome pregnancies is significantly higher compared to that of control and other trisomic pregnancies; n=number of patients, **, p<0.01

Figure 6:
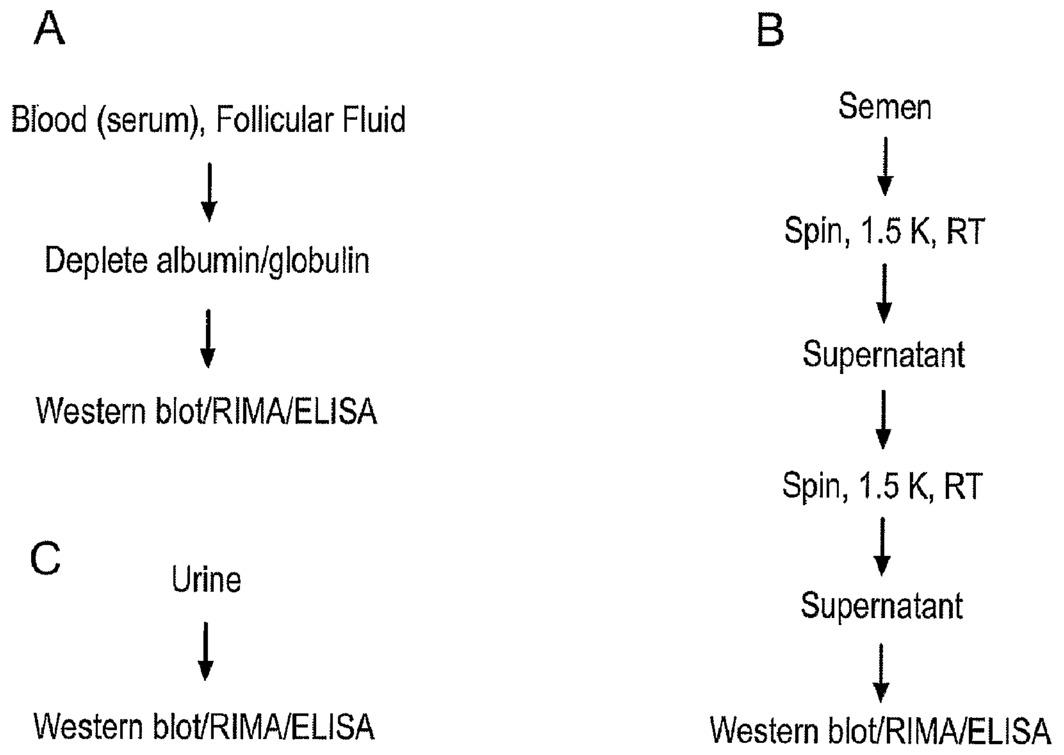
FIG. 6 shows schematically diagnostic test protocols for detecting sLHCGR in body fluids.

FIG. 6 shows schematically diagnostic test protocols for detecting sLHCGR in body fluids such as serum, seminal plasma, urine and follicular fluid.

As shown in FIG. 6A, blood or follicular fluid may be obtained from a patient and placed in a suitable diagnostic container separated from the patient's body. The sample is then depleted of albumin and globulin and subjected to Western blotting or another suitable technique for separating the proteins of the sample according to their molecular weight and providing the proteins in a form (preferably immobilised) suitable for subsequent assaying.

The resultant proteins are then assayed using a suitable specific binding assay to determine the presence or absence, preferably in a quantitative or semi-quantitative manner, of an LHCGR protein.

As shown in FIG. 6B, semen may be obtained from a patient and placed in a suitable diagnostic container separated from the patient's body. The sample is then centrifuged at a rotation speed sufficient to separate the spermatozoa and other separable material and leave a supernatant of seminal plasma (e.g. 1500×g or 1.5K). The supernatant is then separated off and recentrifuged (e.g. under the same conditions). The resulting supernatant is then separated off and subjected to Western blotting or another suitable technique for separating the proteins of the sample according to their molecular weight and providing the proteins in a form (preferably immobilised) suitable for subsequent assaying.

The resultant proteins are then assayed using a suitable specific binding assay to determine the presence or absence, preferably in a quantitative or semi-quantitative manner, of an LHCGR protein.

As shown in FIG. 6C, urine may be obtained from a patient and placed in a suitable diagnostic container separated from the patient's body. The sample is then subjected to Western blotting or another suitable technique for separating the proteins of the sample according to their molecular weight and providing the proteins in a form (preferably immobilised) suitable for subsequent assaying.

The resultant proteins are then assayed using a suitable specific binding assay to determine the presence or absence, preferably in a quantitative or semi-quantitative manner, of an LHCGR protein.

Any suitable protein assay protocol having the necessary degree of specificity to the soluble LHCGR protein of the present invention may be used. Preferred assay protocols include RIMA (radio-immunometric assay) and ELISA (enzyme-linked immunosorbent assay). Specific binding assays are well known in the art and detailed discussion is not required here.

Figure 7:
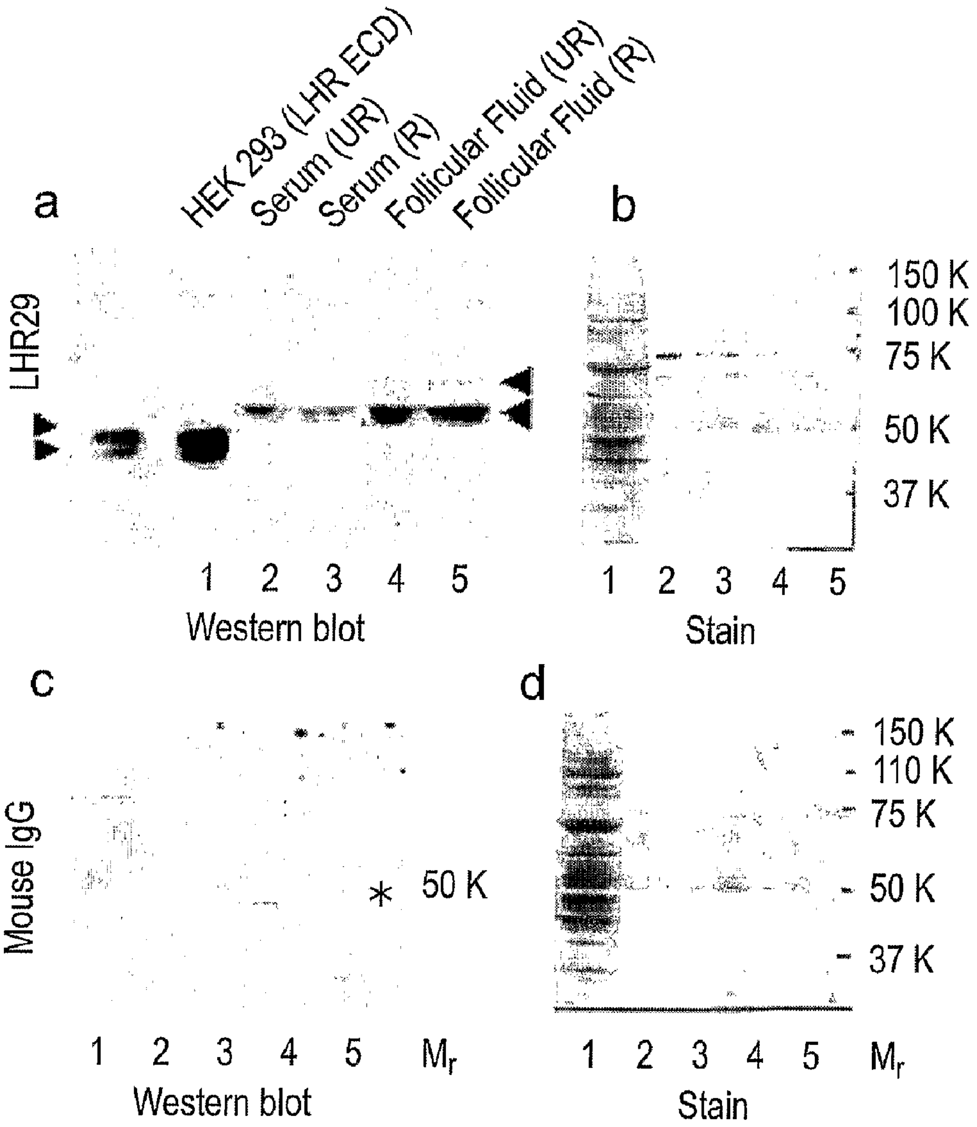
FIG. 7 shows Western blots of isolated LHCGR proteins obtained from various sources, as well as reference materials, under the immunostaining protocols: LHR29 anti-LHCGR antibody (FIG. 7*a*); LHR29 anti-LHCGR antibody followed by staining with Coomassie blue and destaining (FIG. 7*b*); non-specific mouse IgGG antibody (FIG. 7*c*); non-specific mouse IgG antibody followed by staining with Coomassie blue and destaining (FIG. 7*d*); LHR29 anti-LHCGR antibody (FIG. 7*e*, lanes 1 and 2); and MCA 329 anti-hCG 13 monoclonal antibody (FIG. 7*e*, lanes 3 to 6)
Figure 7:
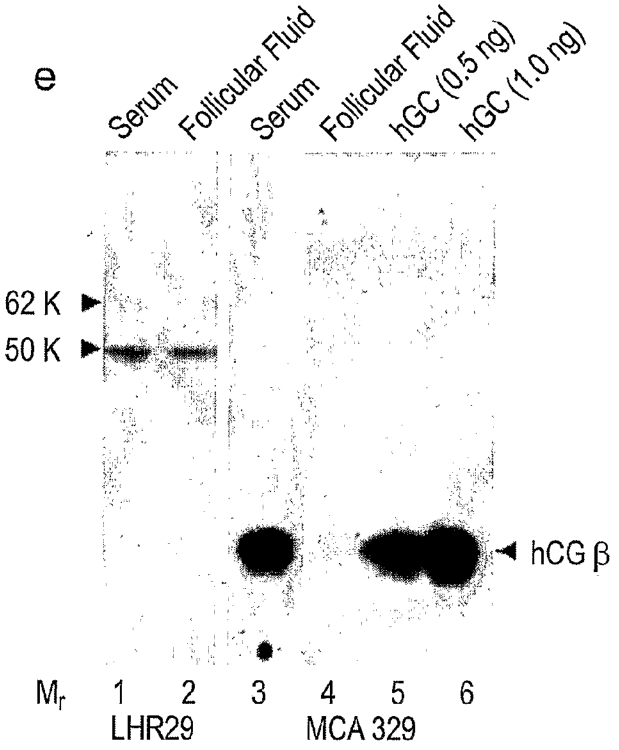

FIG. 7 shows the results of tests to show that sLHCGR complexes with hCG in serum and follicular fluid.

sLHCGR-hCG complex was isolated from pregnant human serum (12 wks gestation) and follicular fluid by affinity purification carried out using activated PreACT™ Agarose ALD chromatography matrix (Novagen Inc. Wisconsin, USA). The monoclonal antibody LHR 29 (2.5 mg/ml) was coupled to the matrix in the presence of sodium cyanoborohydride. Affinity purification was performed according to the protocol provided by the kit. The bound proteins were eluted with 100 mM Glycine, pH 2.8. The neutralised eluted proteins were concentrated using Vivaspin 500 columns (Vivascience AG, Hannover, Germany).

The affinity purified and concentrated materials were resolved in 8% polyacrylamide-SDS gels, electro-transferred to PVDF (Immobilon P, Millipore, Watford, UK).

A portion of each purified material was subjected to disulfide bond reduction using 100 mM 1,4-dithiothreitol (DTT).

The resultant four samples were serum isolate (unreduced), assigned to lane 2 of FIGS. 7*a* to 7*d* (indicated as "Serum (UR)"); serum isolate (reduced), assigned to lane 3 of FIGS. *7a* to *7d* (indicated as "Serum (R)"); follicular fluid isolate (unreduced), assigned to lane 4 of FIGS. *7a* to *7d* (indicated as "Follicular Fluid (UR)"); and follicular fluid isolate (reduced), assigned to lane 5 of FIGS. *7a* to *7d* (indicated as "Follicular Fluid (R)").

A reference sample of a recombinant LHCGR epitope containing protein was obtained from HEK 293 (LHR ECD), a cell line expressing N-terminal 362 aminoacid residues of human LHCGR (kindly provided by Prof. Axel Themmen, Erasmus Universty, Rotterdam, The Netherlands). In the expression vector, LHR ECD is fused to a tag peptide (YPY-DVPDYA) from the hemagglutinin 1 (HA1) epitope of influenza virus and tetracycline-inducible promoter. The reference sample was assigned to lane 1 of FIGS. *7a* to *7d*. As shown in FIG. *7a* (lane 1), two bands are visible from HEK 293 extract. These bands (at about 48K and 44K, variance probably caused by differences in glycosylation) are known to be LHCGR specific because they are also recognised by 12CA5 anti-HA1 antibody antibody in Western blots and are inducible by tetracyclin. The lane to the left of lane 1 in FIG. *7a* is a shorter exposure of lane 1.

The samples thus obtained were immunostained with primary)(1° antibodies as indicated (FIG. *7a*=mouse monoclonal LHR 29; and FIG. *7c*=control mouse immunoglobulin G (IgG, Sigma, St. Louis, Mo., USA) having no affinity for LHCGR). The secondary antibody)(2° for both blots was a goat anti-mouse IgG (H+L)-HRP conjugated (Chemicon International, Temecula, Calif., USA). Following immunostaining, the dried blots were stained with 0.25% Coomassie brilliant blue in 40% methanol and destained (FIG. *7b* and FIG. *7d*).

Affinity-purified samples of the complex obtained from serum and follicular fluid were subjected to the further tests, the results of which are shown in FIG. *7e*.

In FIG. *7e*, lane 1 relates to an affinity purified sample obtained from serum and immunostained with LHR 29 (anti LHCGR); lane 2 relates to an affinity purified sample obtained from follicular fluid and immunostained with LHR 29; lane 3 relates to the same affinity purified sample obtained from serum (as lane 1) and immunostained with MCA 329 (anti-hCG β monoclonal antibody, Serotec, Oxford, UK); lane 4 relates to the same affinity purified sample (as lane 2) obtained from follicular fluid and immunostained with MCA 329; lane 5 relates to a reference sample containing 0.5 ng of recombinant hCG standard (Sigma, St. Louis, Mo., USA) in a comparable medium; and lane 6 relates to a second reference sample containing 1.0 ng of recombinant hCG standard (Sigma, St. Louis, Mo., USA) in a comparable medium.

Notably, in addition to the major 50 K ($M_r$), affinity purification revealed a minor ($M_r$, 62 K) LHCGR-specific band indicated by arrows in FIG. *7a* and FIG. *7e*. The * in FIG. *7c* is a barely visible non-specific band reacting with the control IgG. This band (of $M_r$ 47 K in FIG. *7a* (lanes 2-5) and FIG. *7e* (lanes 1-2)) is migrating just below the major 50 K specific band.

The results shown in FIG. 7 show that the samples derived from the pregnant serum and the follicular fluid contained material which is a complex containing both soluble LHCGR and hCG.

Figure 8:
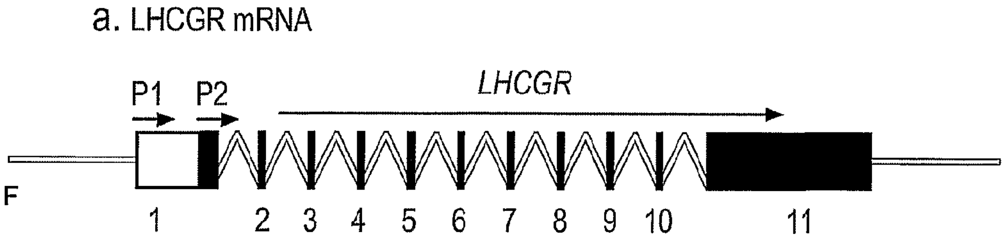
FIG. 8 shows (a) the arrangement of the full human LHCGR gene (exons); (b) the full human LHCGR cDNA sequence; and (c) the full human LHCGR protein sequence, as described.
Figure 8:
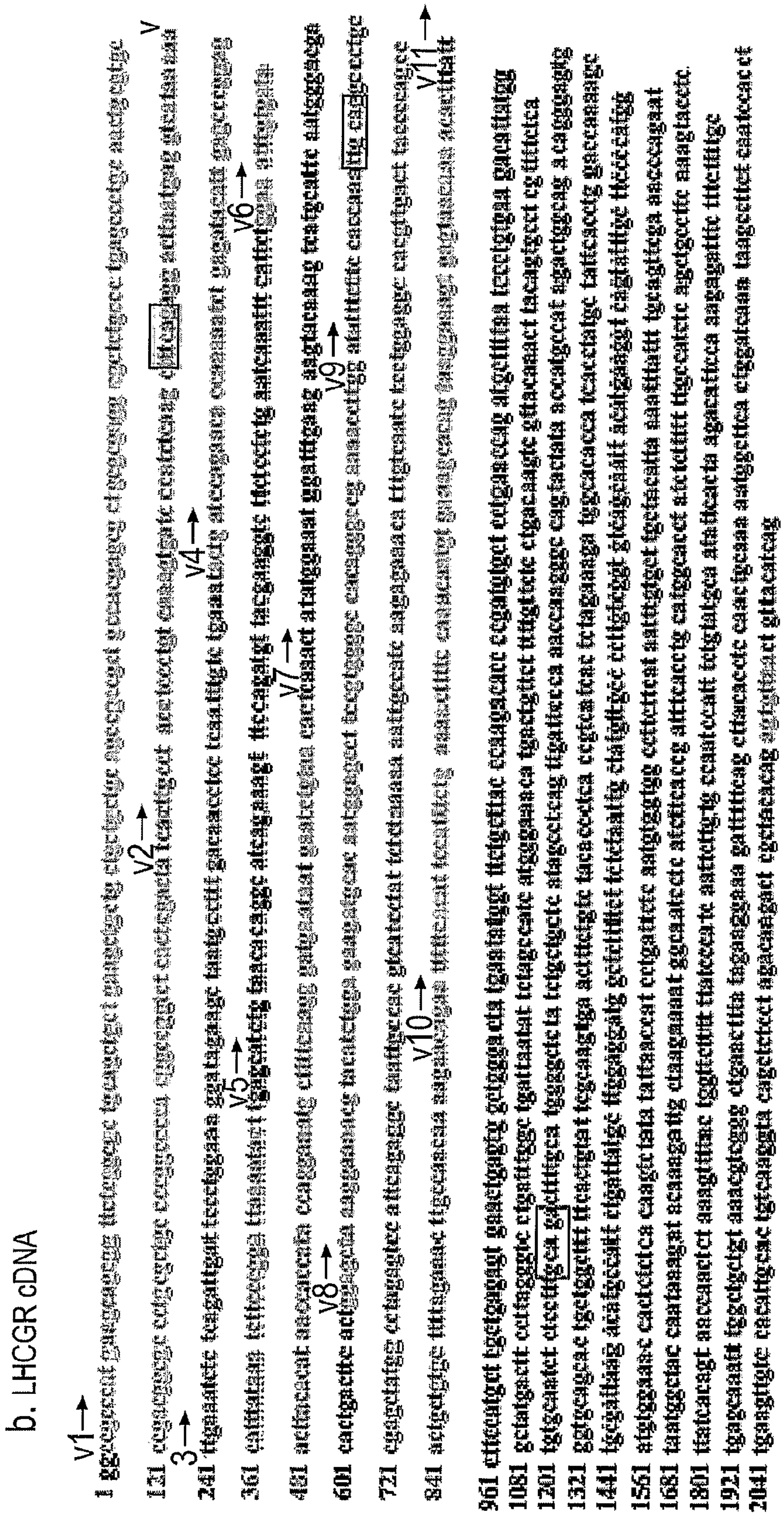

FIG. 8a shows the human LHCGR gene (exons), which is known to be located at chromosome 2p21 (HUGO GeneID: 3973, Locus tag: HGNC:6585). The LHCGR gene is about 70 kb and has 11 exons which are separated by 10 introns.

At least six LHCGR mRNA variants arising from alternative splicing have been reported. Deletions of exons 8, 9, 10 and part of exon 11 are most common.

FIG. 8b and SEQ. ID. NO. 4 show the mature LHCGR cDNA sequence (GenBank sequence ID: NM 000233). The start of each exon is marked by the letter v above the sequence, the point of the v signifying the change of exon. The number of the exon starting at that point is shown to the right of each v. About half of the cDNA is made up of exons 1-10 and the other half by exon 11. The potential alternative splice sites (ttgcag) within the cDNA are shown.

FIG. 8c and SEQ. ID NO. 3 show the full-length LHCGR protein (SwissProt ID P22888; NCBI reference sequence number NP 0000224). In addition to residues 1-24 signal peptide, the LHCGR protein has three domains: the extracellular domain (EC domain) consists of N-terminal ~340 residues and is primarily responsible for LH/hCG hormone binding (this region is coded by exons 1-10 and a part of exon 11); the transmembrane (TM) domain, anchored to cell membrane; and a small intracellular (IC) domain which binds to G-proteins for signal transduction.

The region (amino acid residues 75-406, shown in brackets { }) has been used to produce mouse monoclonal antibodies LHR29 and LHR74 where each recognizes different epitopes. In addition, a polyclonal rabbit antibody raised against residues 210-229 (shown in bold in FIG. 8) was used to verify the results obtained with mouse monoclonal antibody.

As previously mentioned, a number of polymorphisms have been observed in exons 1 (insertion of aminoacids IQ at residue 18 being most common), in exons 8, 10 and 11. In addition, a large relatively number of activating mutations which are primarily restricted to exon 11 (for example, A373V, M398T, L457R, I542L, D564G, A568V, M571I, A572V, I575L, T577I, D578G/Y/H/E, C581R) and inactivating mutations (for example, insertion at residue 18-LLKLLLLLQLQ, deletions in exons 8, 10) and single nucleotide mutations at C131R, F194V, C343S, E354K, W491X, C543R, C545X, R554X, A593P, S616Y and I625K.

Discussion of the Test Data

The above test data strongly indicate that the affinity purified MW 50-62 K protein from pregnant human serum represents approximately 450-470 residues of the N-terminal sequences of human LH/hCG receptor protein (LHCGR). This is the isolatable, soluble, protein molecule newly recognised and used according to the present invention.

The 50K protein in albumin-globulin depleted human pregnant serum can be immunodetected by a monoclonal antibody (LHR29) which has been extensively characterised by Prof. Edwin Milgrom's lab (INSERM, Paris, France). LHR29 monoclonal antibody was originally obtained by immunizing mice with the purified recombinant human receptor extracellular domain (aa 75-406) expressed in *Escherichia coli*. The specificity of the antibody was verified by its ability to immunoprecipitate recombinant receptor and immunopurify $^{125}$I-hCG-receptor complexes from transfected cells, Western-blot with the immunogen, immunocytochemistry of cells transfected by either the cloned receptor or a mock vector. Patterns obtained by immunohistochemistry of human testis matched with results expected for a transmembrane receptor specific of Leydig cells (Meduri G, Charnaux N, Loosfelt H, Jolivet A, Spyratos F, Brailly S & Milgrom E. Luteinizing hormone/human chorionic gonadotropin receptors in breast cancer. *Cancer Research* 1997, 57: 857-864). In addition, LHCGR isoforms in human placental extract have recently been reported by an independent study with a different monoclonal antibody, anti-LHR mAb clone 3B5 (Bukovsky A, Indrapichate K, Fujiwara H, Cekanova M, Ayala M E, Dominguez R, Caudle M R, Wimalsena J, Elder R F, Copas P, Foster J S, Fernando R1, Henley D C & Upadhyaya N B. Multiple luteinizing hormone receptor (LHR) protein variants, interspecies reactivity of anti-LHR mAb clone 3B5, subcellular localization of LHR in human placenta, pelvic floor and brain, and possible role for LHR in the development of abnormal pregnancy, pelvic floor disorders and Alzheimer's disease. Reproductive Biology and Endocrinology 2003, 1: 46).

The specificity of LHR 29 has been further verified by employing two other antibodies which recognize two different epitopes of LHCGR. LHR74, a mouse monoclonal antibody and a rabbit polyclonal antibody (BP 605, Acris, Germany) against residues 210-229 ($H_2N$-HLEKMHNG AFRGATGPKTLD-COOH). Both antibodies, unlike corresponding primary control IgGs, specifically stain affinity purified 50K sLHCGR in Western blots (see FIG. 7).

The 50-62K LHCGR binds hCG: Purification of the pregnant serum and follicular fluid through an affinity matrix coupled to LHR29 results in isolation of sLHCGR (50-62K) bound to hCG (FIG. 5). Affinity matrix coupled to recombinant hCG and buffer controls failed to purify the sLHCGR from human serum and follicular fluid (data not shown). This shows that sLHCGR is bound to the ligand hCG in the serum and follicular fluid. It has been well established by numerous laboratories that the extracellular domain (ECD) of LHCGR binds to the hormone. Therefore, based on epitope interaction with three antibodies described above and affinity data, it is credibly seen that the 50 K sLHCGR identified in this application represents 450-470 residues of the N-terminal half of the mature human LHCGR protein.

As outlined above, LH and hCG have distinctly different functions in human reproduction, although both hormones interact with a common receptor, LHCGR. Of the multiple LHCGR isoforms produced by target cells, the mature full-length receptor (mLHCGR) is anchored to the cell membrane while other isoforms remain inside the cell. However, we have discovered that at least one LHCGR isoform is released from the cells and can be detected in the blood and the ovarian follicular fluid. This soluble receptor (termed sLHCGR) can bind hormone but cannot deliver hormone function. The sLHCGR concentration in Down's syndrome pregnancies is significantly higher compared to that of age-matched control pregnancies (FIG. 5), and the finding of the sLHCGR protein underlying the present invention makes available other diagnostic and therapeutic methods.

The above broadly describes the present invention without limitation. Variations and modifications as will be readily apparent to those of ordinary skill in this art are intended to be within the scope of this application and subsequent patent(s).

REFERENCES

1. McFarland K C, Sprengel R, Phillips H S, Kohler M, Rosemblit N, Nikolics K, Segaloff D L, Seeburg P H. Lutropin-choriogonadotropin receptor: an unusual member of the G protein-coupled receptor family. Science 245: 494-499, 1989.
2. Loosfelt H, Misrahi M, Atger M, Salesse R, Vu Hai-Luu Thi M T, Jolivet A, Guiochon-Mantel A, Sar S, Jallal B, Garnier J, et al. Cloning and sequencing of porcine LH-hCG receptor cDNA: variants lacking transmembrane domain. Science 245:525-528, 1989.
3. Rousseau-Merck M F, Misrahi M, Atger M, Loosfelt H, Milgrom E, Berger R. Localization of the human luteinizing hormone/choriogonadotropin receptor gene (LHCGR) to chromosome 2p21. Cytogenet Cell Genet. 54:77-79, 1990.
4. Ascoli M, Fanelli F, Segaloff D L. The lutropin/choriogonadotropin receptor, a 2002 perspective. Endocr Rev. 23:141-174, 2002.
5. Tsai-Morris C H, Buczko E, Wang W, Dufau M L. Intronic nature of the rat luteinizing hormone receptor gene defines a soluble receptor subspecies *with* hormone binding activity. J Biol. Chem. 265:19385-19398, 1990.
6. VuHai-LuuThi M T, Misrahi M, Houllier A, Jolivet A, Milgrom E. Variant forms of the pig lutropin/choriogonadotropin receptor. Biochemistry. 31:8377-8383, 1992.
7. You S, Kim H, El Halawani M E, Foster D N. Three different turkey luteinizing hormone receptor (tLH-R) isoforms II: characterization of differentially regulated tLH-R messenger ribonucleic acid isoforms in the ovary. Biol Reprod. 62:117-124, 2000.
8. Kolena J, Sebokova E, Horkovics-Kovats S. LH/hCG receptor in pig follicular fluid. Endocrinol Exp. 20:339-348, 1986.
9. Moncayo H, Moncayo R, Benz R, Wolf A, Lauritzen C. Ovarian failure and autoimmunity. Detection of autoantibodies directed against both the unoccupied luteinizing hormone/human chorionic gonadotropin receptor and the hormone-receptor complex of bovine corpus luteum. J Clin Invest. 84:1857-1865, 1989.
10. Venencie P Y, Meduri G, Pissard S, Jolivet A, Loosfelt H, Milgrom E, Misrahi M. Luteinizing hormone/human chorionic gonadotrophin receptors in various epidermal structures. Br J. Dermatol. 141:438-446, 1999.
11. Meduri G, Charnaux N, Loosfelt H, Jolivet A, Spyratos F, Brailly S, Milgrom E. Luteinizing hormone/human chorionic gonadotropin receptors in breast cancer. Cancer Res. 57:857-864, 1997.
12. Tao Y X, Lei Z M, Rao C V. Seminal vesicles are novel sites of luteinizing hormone/human chorionic gonadotropin-receptor gene expression. J. Androl. 19:343-347, 1998.
13. Konishi I, Koshiyama M, Mandai M, Kuroda H, Yamamoto S, Nanbu K, Komatsu T, Matsushita K, Rao C V, Mori T. Increased expression of LH/hCG receptors in endometrial hyperplasia and carcinoma in anovulatory women. Gynecol Oncol. 65:273-280, 1997.
14. Tao Y X, Bao S, Ackermann D M, Lei Z M, Rao C V. Expression of luteinizing hormone/human chorionic gonadotropin receptor gene in benign prostatic hyperplasia and in prostate carcinoma in humans. Biol Reprod. 56:67-72, 1997.
15. Pabon J E, Bird J S, Li X, Huang Z H, Lei Z M, Sanfilippo J S, Yussman M A, Rao C V. Human skin contains luteinizing hormone/chorionic gonadotropin receptors. J Clin Endocrinol Metab. 81:2738-2741, 1996.
16. Pabon J E, Li X, Lei Z M, Sanfilippo J S, Yussman M A, Rao C V. Novel presence of luteinizing hormone/chorionic gonadotropin receptors in human adrenal glands. J Clin Endocrinol Metab. 81:2397-2400, 1996.
17. Singh M, Zuo J, Li X, Ambrus G, Lei Z M, Yussman M A, Sanfilippo J S, Rao C V. Decreased expression of functional human chorionic gonadotropin/luteinizing hormone receptor gene in human uterine leiomyomas. Biol Reprod. 53:591-597, 1995.
18. Lin J, Lojun S, Lei Z M, Wu W X, Peiner S C, Rao C V. Lymphocytes from pregnant women express human chorionic gonadotropin/luteinizing hormone receptor gene. Mol Cell Endocrinol. 111:R13-17, 1995.
19. Zuo J, Lei Z M, Rao C V. Human myometrial chorionic gonadotropin/luteinizing hormone receptors in preterm and term deliveries. J Clin Endocrinol Metab. 79:907-911, 1994.

20. Eblen A, Bao S, Lei Z M, Nakajima S T, Rao C V. The presence of functional luteinizing hormone/chorionic gonadotropin receptors in human sperm. J Clin Endocrinol Metab. 86:2643-2648, 2001.
21. Abdallah M A, Lei Z M, Li X, Greenwold N, Nakajima S T, Jauniaux E, Rao ChV. Human fetal nongonadal tissues contain human chorionic gonadotropin/luteinizing hormone receptors. J Clin Endocrinol Metab. 89:952-956, 2004.
22. Bukovsky A, Indrapichate K, Fujiwara H, Cekanova M, Ayala M E, Dominguez R, Caudle M R, Wimalsena J, Elder R F, Copas P, Foster J S, Fernando R1, Henley D C, Upadhyaya N B. Multiple luteinizing hormone receptor (LHR) protein variants, interspecies reactivity of anti-LHR mAb clone 3B5, subcellular localization of LHR in human placenta, pelvic floor and brain, and possible role for LHR in the development of abnormal pregnancy, pelvic floor disorders and Alzheimer's disease. Reprod Biol Endocrinol. 1:46, 2003.
23. Bozon V, Couture L, Pajot-Augy E, Richard F, Remy J J, Salesse R. Rescue of intracellularly trapped lutropin receptor exodomain by endodomain and reconstitution of a functional membrane receptor: interaction between exo- and endodomains. Protein Expr Purif. 25:114-123, 2002.
24. Funaro A, Sapino A, Ferranti B, Horenstein A L, Castellano I, Bagni B, Garotta G, Malavasi F. Functional, structural, and distribution analysis of the chorionic gonadotropin receptor using murine monoclonal antibodies. J Clin Endocrinol Metab. 88:5537-5546, 2003.
25. Rozzell T G, Wang H, Liu X, Segaloff D L. Intracellular retention of mutant gonadotropin receptors results in loss of hormone binding activity of the follitropin receptor but not of the lutropin/choriogonadotropin receptor. Mol. Endocrinol. 9:1727-1736, 1995.
26. Bruch R C, Thotakura N R, Bahl O P. The rat ovarian lutropin receptor. Purification, hormone binding properties, and subunit composition. J Biol. Chem. 261:9450-9460, 1986.
27. Wimalasena J, Schwab S, Dufau M L. Soluble luteinizing hormone/human chorionic gonadotropin receptors of the rat ovary: comparative studies of water- and detergent-soluble receptors. Endocrinology 113:618-624, 1983.
28. Wimalasena J, Dufau M L. Water-soluble gonadotropin receptors of the rat ovary. Endocrinology 110:1004-1012, 1982.
29. Vuhai-Luuthi M T, Jolivet A, Jallal B, Salesse R, Bidart J M, Houllier A, Guiochon-Mantel A, Garnier J, Milgrom E. Monoclonal antibodies against luteinizing hormone receptor. Immunochemical characterization of the receptor. Endocrinology 127:2090-2098, 1990.
30. Hipkin R W, Sanchez-Yague J, Ascoli M. Identification and characterization of a luteinizing hormone/chorionic gonadotropin (LH/CG) receptor precursor in a human kidney cell line stably transfected with the rat luteal LH/CG receptor complementary DNA. Mol. Endocrinol. 6: 2210-2218, 1992.
31. Min L, Ascoli M. Effect of activating and inactivating mutations on the phosphorylation and trafficking of the human lutropin/choriogonadotropin receptor. Mol. Endocrinol. 14:1797-1810, 2000.
32. Remy J J, Nespoulous C, Grosclaude J, Grebert D, Couture L, Pajot E, Salesse R. Purification and structural analysis of a soluble human chorionogonadotropin hormone-receptor complex. J Biol. Chem. 276:1681-1687, 2001.
33. Osuga Y, Kudo M, Kaipia A, Kobilka B, Hsuch A J. Derivation of functional antagonists using N-terminal extracellular domain of gonadotropin and thyrotropin receptors. Mol. Endocrinol. 11:1659-1668, 1997.
34. Kellokumpu S, Rajaniemi H. Involvement of plasma membrane enzymes in the proteolytic cleavage of luteinizing hormone receptor. Endocrinology 116:707-714, 1985.
35. Kremer H, Kraaij R, Toledo S P, Post M, Fridman J B, Hayashida C Y, van Reen M, Milgrom E, Ropers H H, Mariman E, et al. Male pseudohermaphroditism due to a homozygous missense mutation of the luteinizing hormone receptor gene. Nat. Genet. 9:160-164, 1995.
36. Jauniaux E, Bao S, Eblen A, Li X, Lei Z M, Meuris S, Rao C V. HCG concentration and receptor gene expression in placental tissue from trisomy 18 and 21. Mol Hum Reprod. 6: 5-10, 2000.
37. Maynard S E, Min J Y, Merchan J, Lim M I, Li J, Mondal S, Libermann T A, Morgan J P, Sellke F W, Stillman I E, Epstein F H, Sukhatme V P, Karumanchi S A. Excess placental soluble fins-like tyrosine kinase 1 (sFlt1) may contribute to endothelial dysfunction, hypertension, and proteinuria in preeclampsia. J Clin Invest. 111:649-658, 2003.
38. Thadhani R, Mutter W P, Wolf M, Levine R J, Taylor R N, Sukhatme V P, Ecker J, Karumanchi S A. First trimester placental growth factor and soluble fins-like tyrosine kinase 1 and risk for preeclampsia. J Clin Endocrinol Metab. 89:770-775, 2004.
39. Austgulen R, Liabakk N B, Lien E, Espevik T. Increased levels of soluble tumor necrosis factor-alpha receptors in serum from pregnant women and in serum and urine samples from newborns. Pediatr Res. 33:82-87, 1993
40. Pitard V, Lorgeot V, Taupin J L, Aubard Y, Praloran V, Moreau J F. The presence in human serum of a circulating soluble leukemia inhibitory factor receptor (sgp190) and its evolution during pregnancy. Eur Cytokine Netw. 9:599-605, 1998.
41. Nuamah M A, Sagawa N, Yura S, Mise H, Itoh H, Ogawa Y, Nakao K, Fujii S. Free-to-total leptin ratio in maternal plasma is constant throughout human pregnancy. Endocr J. 50:421-428, 2003.
42. Lewandowski K, Horn R, O'Callaghan C J, Dunlop D, Medley G F, O'Hare P, Brabant G. Free leptin, bound leptin, and soluble leptin receptor in normal and diabetic pregnancies. J Clin Endocrinol Metab. 84:300-306, 1999.

The invention claimed is:

1. A method of diagnosing susceptibility to a condition selected from human infertility conditions, egg maturation disorders, Down's syndrome and pre-eclampsia, in a subject, which comprises:

(a) assaying a sample of body fluid obtained from the subject to measure levels of:
   (i) a soluble LHCGR polypeptide having the amino acid sequence of SEQ ID No. 1; or
   (ii) a ligand capable of binding to said polypeptide of (i) wherein the ligand is a hormone; or
   (iii) a complex of said polypeptide of (i) and said ligand of (ii); and (b) comparing levels measured in (a) to levels measured in a normal condition, wherein:
   (1) an increase in the measured level of said polypeptide of (i) relative to the measured level in the normal condition is indicative of susceptibility to said condition; or
   (2) an elevation in the measured level of said complex of (iii) relative to the measured level in the normal condition is indicative of susceptibility to said condition; or
   (3) a decrease in the measured level of said ligand of (ii) relative to the measured level in the normal condition is indicative of susceptibility to said condition.

2. A method of diagnosing a condition selected from human infertility conditions, egg maturation disorders, Down's syndrome and pre-eclampsia, in a subject, which comprises:

(a) assaying the sample of body fluid obtained from the subject to measure levels of:
   (i) a soluble LHCGR polypeptide having the amino acid sequence of SEQ ID No. 1; or
   (ii) a ligand capable of binding to said polypeptide of (i) wherein the ligand is a hormone; or
   (iii) a complex of said polypeptide of (i) and said ligand of (ii); and (b) comparing levels measured in (a) to levels measured in a normal condition, wherein:
   (1) an increase in the measured level of said polypeptide of (i); relative to the measured level in the normal condition is indicative of the existence of said condition; or (2) an elevation in the measured level of said complex of (iii) relative to the measured level in the normal condition is indicative of the existence of said condition; or (3) a decrease in the measured level of said ligand of (ii) relative to the measured level in the normal condition is indicative of the existence of said condition.

3. A method according to claim 2, wherein the body fluid is serum or urine.

4. A method of diagnosing a risk of male or female infertility or difficulty to conceive; or impaired egg maturation; or Down's syndrome; or pre-eclampsia; or a susceptibility thereto; in a human or non-human animal patient, which comprises:

(a) assaying a sample of body fluid removed from the patient to measure levels of a soluble LHCGR polypeptide having the amino acid sequence of SEQ. ID No. 1 or an antibody thereto; and (b) comparing levels measured in (a) to levels measured in a normal condition, wherein an increase in the levels measured in (a) relative to the measured levels in the normal condition is indicative of the existence of risk of said condition.

* * * * *

SEQUENCE LISTING

```
<160> NUMBER OF SEQ ID NOS: 4

<210> SEQ ID NO 1
<211> LENGTH: 450
<212> TYPE: PRT
```

-continued

<213> ORGANISM: Homo sapiens

<400> SEQUENCE: 1

```
Met Lys Gln Arg Phe Ser Ala Leu Gln Leu Leu Lys Leu Leu Leu Leu
1               5                   10                  15

Leu Gln Pro Pro Leu Pro Arg Ala Leu Arg Glu Ala Leu Cys Pro Glu
            20                  25                  30

Pro Cys Asn Cys Val Pro Asp Gly Ala Leu Arg Cys Pro Gly Pro Thr
        35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Gly Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365

Ile Asn Ile Leu Ala Ile Met Gly Asn Met Thr Val Leu Phe Val Leu
    370                 375                 380

Leu Thr Ser Arg Tyr Lys Leu Thr Val Pro Arg Phe Leu Met Cys Asn
385                 390                 395                 400
```

-continued

```
Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
            420                 425                 430

Trp Gln Thr Gly Ser Gly Cys Ser Thr Ala Gly Phe Phe Thr Val Phe
        435                 440                 445

Ala Ser
    450


<210> SEQ ID NO 2
<211> LENGTH: 1350
<212> TYPE: DNA
<213> ORGANISM: Homo sapiens

<400> SEQUENCE: 2

ggccgcccat gaagcagcgg ttctcggcgc tgcagctgct gaagctgctg ctgctgctgc      60

agccgccgct gccacgagcg ctgcgcgagg cgctctgccc tgagccctgc aactgcgtgc     120

ccgacggcgc cctgcgctgc cccggcccca cggccggtct cactcgacta tcacttgcct     180

acctccctgt caaagtgatc ccatctcaag ctttcagagg acttaatgag gtcataaaaa     240

ttgaaatctc tcagattgat tccctggaaa ggatagaagc taatgccttt gacaacctcc     300

tcaatttgtc tgaaatactg atccagaaca ccaaaaatct gagatacatt gagcccggag     360

catttataaa tcttcccgga ttaaaatact tgagcatctg taacacaggc atcagaaagt     420

ttccagatgt tacgaaggtc ttctcctctg aatcaaattt cattctggaa atttgtgata     480

acttacacat aaccaccata ccaggaaatg cttttcaagg gatgaataat gaatctgtaa     540

cactcaaact atatggaaat ggatttgaag aagtacaaag tcatgcattc aatgggacga     600

cactgacttc actggagcta aaggaaaacg tacatctgga gaagatgcac aatggagcct     660

tccgtggggc cacagggccg aaaaccttgg atatttcttc caccaaattg caggccctgc     720

cgagctatgg cctagagtcc attcagaggc taattgccac gtcatcctat tctctaaaaa     780

aattgccatc aagagaaaca tttgtcaatc tcctggaggc cacgttgact taccccagcc     840

actgctgtgc ttttagaaac ttgccaacaa aagaacagaa tttttcacat tccatttctg     900

aaaacttttc caaacaatgt gaaagcacag taaggaaagt gagtaacaaa acactttatt     960

cttccatgct tgctgagagt gaactgagtg gctgggacta tgaatatggt ttctgcttac    1020

ccaagacacc ccgatgtgct cctgaaccag atgcttttaa tccctgtgaa gacattatgg    1080

gctatgactt ccttagggtc ctgatttggc tgattaatat tctagccatc atgggaaaca    1140

tgactgttct tttgttctc ctgacaagtc gttacaaact tacagtgcct cgttttctca    1200

tgtgcaatct ctcctttgca gacttttgca tggggctcta tctgctgctc atagcctcag    1260

ttgattccca aaccaagggc cagtactata accatgccat agactggcag acagggagtg    1320

ggtgcagcac tgctggcttt ttcactgtat                                     1350


<210> SEQ ID NO 3
<211> LENGTH: 699
<212> TYPE: PRT
<213> ORGANISM: Homo sapiens

<400> SEQUENCE: 3

Met Lys Gln Arg Phe Ser Ala Leu Gln Leu Leu Lys Leu Leu Leu Leu
1               5                   10                  15

Leu Gln Pro Pro Leu Pro Arg Ala Leu Arg Glu Ala Leu Cys Pro Glu
            20                  25                  30
```

-continued

```
Pro Cys Asn Cys Val Pro Asp Gly Ala Leu Arg Cys Pro Gly Pro Thr
        35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Gly Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365

Ile Asn Ile Leu Ala Ile Met Gly Asn Met Thr Val Leu Phe Val Leu
    370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
            420                 425                 430

Trp Gln Thr Gly Ser Gly Cys Ser Thr Ala Gly Phe Phe Thr Val Phe
        435                 440                 445
```

-continued

```
Ala Ser Glu Leu Ser Val Tyr Thr Leu Thr Val Ile Thr Leu Glu Arg
    450                 455                 460

Trp His Thr Ile Thr Tyr Ala Ile His Leu Asp Gln Lys Leu Arg Leu
465                 470                 475                 480

Arg His Ala Ile Leu Ile Met Leu Gly Gly Trp Leu Phe Ser Ser Leu
                485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
        515                 520                 525

Leu Thr Ile Leu Ile Leu Asn Val Val Ala Phe Phe Ile Ile Cys Ala
    530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
                565                 570                 575

Thr Asp Phe Thr Cys Met Ala Pro Ile Ser Phe Phe Ala Ile Ser Ala
            580                 585                 590

Ala Phe Lys Val Pro Leu Ile Thr Val Thr Asn Ser Lys Val Leu Leu
        595                 600                 605

Val Leu Phe Tyr Pro Ile Asn Ser Cys Ala Asn Pro Phe Leu Tyr Ala
    610                 615                 620

Ile Phe Thr Lys Thr Phe Gln Arg Asp Phe Phe Leu Leu Leu Ser Lys
625                 630                 635                 640

Phe Gly Cys Cys Lys Arg Arg Ala Glu Leu Tyr Arg Arg Lys Asp Phe
                645                 650                 655

Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
        675                 680                 685

Ala Leu Leu Asp Lys Thr Arg Tyr Thr Glu Cys
    690                 695


<210> SEQ ID NO 4
<211> LENGTH: 2120
<212> TYPE: DNA
<213> ORGANISM: Homo sapiens

<400> SEQUENCE: 4

ggccgcccat gaagcagcgg ttctcggcgc tgcagctgct gaagctgctg ctgctgctgc      60

agccgccgct gccacgagcg ctgcgcgagg cgctctgccc tgagccctgc aactgcgtgc     120

ccgacggcgc cctgcgctgc cccggcccca cggccggtct cactcgacta tcacttgcct     180

acctccctgt caaagtgatc ccatctcaag ctttcagagg acttaatgag gtcataaaaa     240

ttgaaatctc tcagattgat tccctggaaa ggatagaagc taatgccttt gacaacctcc     300

tcaatttgtc tgaaatactg atccagaaca ccaaaaatct gagatacatt gagcccggag     360

catttataaa tcttcccgga ttaaaatact tgagcatctg taacacaggc atcagaaagt     420

ttccagatgt tacgaaggtc ttctcctctg aatcaaattt cattctggaa atttgtgata     480

acttacacat aaccaccata ccaggaaatg cttttcaagg gatgaataat gaatctgtaa     540

cactcaaact atatggaaat ggatttgaag aagtacaaag tcatgcattc aatgggacga     600

cactgacttc actggagcta aaggaaaacg tacatctgga gaagatgcac aatggagcct     660

tccgtggggc cacagggccg aaaaccttgg atatttcttc caccaaattg caggccctgc     720
```

-continued

```
cgagctatgg cctagagtcc attcagaggc taattgccac gtcatcctat tctctaaaaa    780
aattgccatc aagagaaaca tttgtcaatc tcctggaggc cacgttgact taccccagcc    840
actgctgtgc ttttagaaac ttgccaacaa aagaacagaa tttttcacat tccatttctg    900
aaaacttttc caaacaatgt gaaagcacag taaggaaagt gagtaacaaa acactttatt    960
cttccatgct tgctgagagt gaactgagtg gctgggacta tgaatatggt ttctgcttac   1020
ccaagacacc ccgatgtgct cctgaaccag atgcttttaa tccctgtgaa gacattatgg   1080
gctatgactt ccttagggtc ctgatttggc tgattaatat tctagccatc atgggaaaca   1140
tgactgttct ttttgttctc ctgacaagtc gttacaaact tacagtgcct cgttttctca   1200
tgtgcaatct ctcctttgca gacttttgca tggggctcta tctgctgctc atagcctcag   1260
ttgattccca aaccaagggc cagtactata accatgccat agactggcag acagggagtg   1320
ggtgcagcac tgctggcttt ttcactgtat tcgcaagtga actttctgtc tacaccctca   1380
ccgtcatcac tctagaaaga tggcacacca tcacctatgc tattcacctg gaccaaaagc   1440
tgcgattaag acatgccatt ctgattatgc ttggaggatg gctcttttct tctctaattg   1500
ctatgttgcc ccttgtcggt gtcagcaatt acatgaaggt cagtatttgc ttccccatgg   1560
atgtggaaac cactctctca caagtctata tattaaccat cctgattctc aatgtggtgg   1620
ccttcttcat aatttgtgct tgctacatta aaatttattt tgcagttcga aacccagaat   1680
taatggctac caataaagat acaaagattg ctaagaaaat ggcaatcctc atcttcaccg   1740
atttcacctg catggcacct atctcttttt ttgccatctc agctgccttc aaagtacctc   1800
ttatcacagt aaccaactct aaagttttac tggttctttt ttatcccatc aattcttgtg   1860
ccaatccatt tctgtatgca atattcacta agacattcca aagagatttc tttcttttgc   1920
tgagcaaatt tggctgctgt aaacgtcggg ctgaacttta tagaaggaaa gatttttcag   1980
cttacacctc caactgcaaa aatggcttca ctggatcaaa taagccttct caatccacct   2040
tgaagttgtc cacattgcac tgtcaaggta cagctctcct agacaagact cgctacacag   2100
agtgttaact gttacatcag                                               2120
```